United States Patent
Illiano et al.

(10) Patent No.: US 10,988,524 B2
(45) Date of Patent: Apr. 27, 2021

(54) MODIFIED RELAXIN B CHAIN PEPTIDES AND THEIR THERAPEUTIC USE

(71) Applicant: Sanofi, Paris (FR)

(72) Inventors: Stéphane Illiano, Paris (FR); Sergio Mallart, Paris (FR); Claire Minoletti-Hochepied, Paris (FR); Frank Marguet, Paris (FR); Olivier Duclos, Paris (FR); Elisabetta Bianchi, Pomezia (IT); Raffaele Ingenito, Pomezia (IT); Paola Magotti, Van løse (DK); Alessia Santoprete, Pomezia (IT)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 16/264,669

(22) Filed: Jan. 31, 2019

(65) Prior Publication Data

US 2019/0233495 A1 Aug. 1, 2019

(30) Foreign Application Priority Data

Jan. 31, 2018 (EP) .................................... 18305092

(51) Int. Cl.
*A61K 38/00* (2006.01)
*C07K 14/64* (2006.01)

(52) U.S. Cl.
CPC .............. *C07K 14/64* (2013.01); *A61K 38/00* (2013.01)

(58) Field of Classification Search
CPC ................................. A61K 38/00; C07K 14/64
USPC ............................................. 514/1.1; 530/300
See application file for complete search history.

(56) References Cited

U.S. PATENT DOCUMENTS

| | | | |
|---|---|---|---|
| 10,081,662 B2* | 9/2018 | Bathgate | ................... A61P 9/00 |
| 2017/0037106 A1* | 2/2017 | Bathgate | ................ C07K 14/64 |
| 2019/0233493 A1* | 8/2019 | Brasseur | ................... A61P 9/12 |

FOREIGN PATENT DOCUMENTS

| WO | WO2015157829 A1 | 10/2015 |
|---|---|---|
| WO | WO2019149780 A1 | 8/2019 |

OTHER PUBLICATIONS

Different fibrosis diseases from Merck Manual, pp. 1-3. Accessed Apr. 28, 2020. (Year: 2020).*
Idiopathic Pulmonary Fibrosis from Merck Manual, pp. 1-3. Accessed Apr. 28, 2020. (Year: 2020).*
Pulmonary Hypertension from Merck Manual, pp. 1-11. Accessed Apr. 28, 2020. (Year: 2020).*
Acute Kidney Injury from Merck Manual, pp. 1-14. Accessed Apr. 28, 2020. (Year: 2020).*
Bathgate R. A. D. et al. (Jan. 1, 2013). "Relaxin Family Peptides and Their Receptors," Physiological Reviews 93(11):405-480.
Del Borgo, M.P. et al. (Sep. 2005). "Conformationally Constrained Single-Chain Peptide Mimics of Relaxin B-Chain Secondary Structure," J. Pept. Sci. 11(9):564-571.
Hossain, M.A. et al. (Jun. 1, 2016, e-pub. Feb. 26, 2016). "A Single-Chain Derivative of the Relaxin Hormone is a Functionally Selective Agonist of the G Protein-Coupled Receptor, RXFP1," Chem. Sci. 7(6):3805-3819.
Hossain, M.A. et al. (Oct. 2014, e-pub. Oct. 1, 2014). "Synthetic Relaxins," Curr. Opin. Chem. Biol. 22:47-55.
Hossain, M.A. et al. (Oct. 28, 2011). "The Minimal Active Structure of Human Relaxin-2", J. Biol. Chem. 286(43):37555-37565.
International Search Report dated Mar. 11, 2019, for PCT Patent Application No. PCT/EP2019/052296, filed Jan. 30, 2019, 6 pages.
Written Opinion of the International Searching Authority dated Mar. 11, 2019, for PCT Patent Application No. PCT/EP2019/052296, filed Jan. 30, 2019, 6 pages.

* cited by examiner

*Primary Examiner* — Julie Ha
(74) *Attorney, Agent, or Firm* — Goodwin Procter LLP

(57) ABSTRACT

Provided is a biologically active single chain Relaxin peptide having the following formula (I): $N_{ter}$-X-$(E)_a$-$X_{10}$-E-G-R-E-$X_{15}$-V-R-$X_{18}$-$X_{19}$-I-$X_{21}$-$X_{22}$-E-G-$X_{25}$-S-$X_{27}$-$X_{28}$-$X_{29}$-$X_{30}$-R-$(X_{32})_b$-$(X_{33})_c$-$(X_{34})_d$-$NH_2$-$C_{ter}$. Also provided is a p

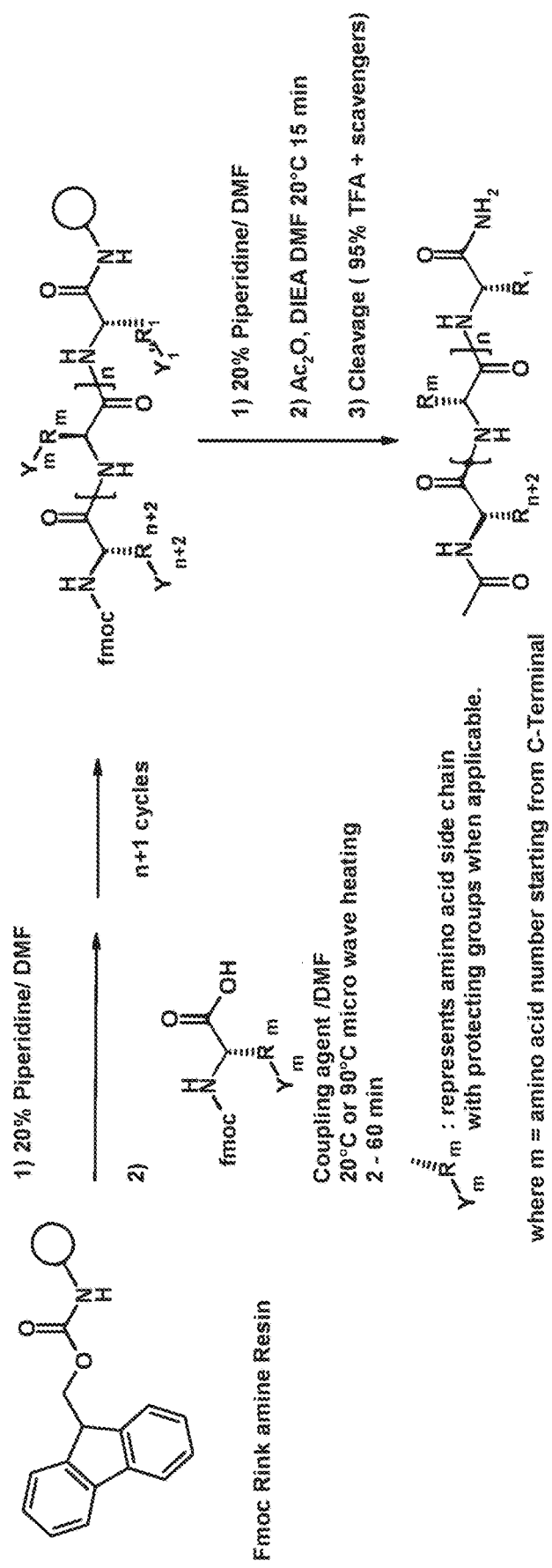
FIGURE

MODIFIED RELAXIN B CHAIN PEPTIDES AND THEIR THERAPEUTIC USE

CROSS REFERENCE TO RELATED APPLICATIONS

This application claims the priority benefit of E.P. Application No. EP18305092.1, filed Jan. 31, 2018, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952031300seqlist.txt, date recorded: Jan. 31, 2019, size: 68 KB).

FIELD OF THE INVENTION

The present invention relates to peptides analogues of the B-chain of Relaxin-2 able to activate the RXFP1 receptor.

Moreover, the present invention provides pharmaceutical compositions comprising at least said peptides, and a peptide or pharmaceutical composition thereof according to the invention for its use as a medicament, and in particular for its use in the treatment and/or prevention of various diseases or conditions implicating the RXFP1 receptor, more particularly a disease or condition selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;

the group consisting of heart and vascular diseases, in particular from the group consisting of acute or chronic heart failure, systolic or diastolic heart failure, coronary artery disease, atherosclerosis, microvascular angina and cardiovascular complication of diabetes and/or the group consisting of renal failures, in particular renal dysfunction in cirrhosis; chronic kidney disease and acute kidney injury.

BACKGROUND OF THE INVENTION

Human Relaxin-2 (H2 Relaxin) is a 6-kDa peptidic hormone of 53 amino acids. Its structure consists of two separate polypeptide chains, i.e. H2 Relaxin chain A (SEQ ID NO: 60) and H2 Relaxin chain B (SEQ ID NO: 61) cross-linked by two disulfide (S—S) bonds, with a third S-S intra-chain bond located in the A chain as follows:

```
H2 Relaxin A chain:
                                  (SEQ ID NO: 60)
H-Gln-Leu-Tyr-Ser-Ala-Leu-Ala-Asn-Lys-Cys*-

Cys**-His-Val-Gly-Cys*-Thr-Lys-Arg-Ser-Leu-

Ala-Arg-Phe-Cys***-OH

H2 Relaxin B chain:
                                  (SEQ ID NO: 61)
H-Asp-Ser-Trp-Met-Glu-Glu-Val-Ile-Lys-Leu- Cys-Gly-Arg-Glu-Leu-Val-Arg-Ala-Gln-Ile- Ala-Ile-Cys*-Gly-Met-Ser-Thr-Trp-Ser-OH
``` wherein Cys*, Cys and Cys* indicate the disulfide bonds between Cysteines with same label.

Relaxin-2 is a naturally occurring peptide hormone produced by corpus luteum with a peak in the circulation during the first trimester of pregnancy of a woman. Relaxin-2 belongs to the insulin-like peptide family which members exert numerous effects after binding to different kinds of receptors, classified as Relaxin family peptide (RXFP) receptors (RXFP1, RXFP2, RXFP3, and RXFP4).

RXFP1 is the main receptor for Relaxin. RXFP1 contains a large extracellular domain with a single low-density lipoprotein class A (LDLa) module at the amino terminus and 10 extracellular leucine-rich repeat domains (LRRs), followed by 7 transmembrane (7TM) helical domains. The LDLa module of RXFP1 is joined to the LRR domain via a 32-residue linker.

Activation of RXFP1 is a complex multistep process. Previous studies have demonstrated that Arg13, Arg17 and Ile20, of the arginine cassette (RxxxRxxI/V, where x is any residue; (SEQ ID NO:67)) of the H2 Relaxin B-chain, bind to Asp231, Asp279, Glu233 and Glu277 located on LRR4-8 of the LRR domain of RXFP1. Ligand binding alone is not sufficient to activate the receptor. Truncation or substitution of the LDLa module results in an inactive receptor despite binding to the extracellular domain. A study (Bruell, S. et al., Front. Endocrinol. (Lausanne) 4, 171 (2013)), swapping the LDLa modules of RXFP1 and RXFP2 highlighted the role of the linker in receptor activation. The LRRs (high affinity site) and the first exoloops (low affinity sites) of the transmembrane domains participate in Relaxin binding, whereas the LDLa module is required for receptor activation involving exoloop 2 (Sethi A. et al. Nature Communications (2016)).

In some species, Relaxin can also activate RXFP2, the native leucine-rich repeat containing GPCR for the insulin-like peptide 3 (INSL3). This suggests that a potential cross reactivity might be associated with Relaxin various biological activities, even though there is currently no evidence of a physiological role for Relaxin acting solely through RXFP2.

Recent published data showed that there are interspecies differences in the capacity of agonists to activate RXFP1 with a specific difference in the ECL3 domain between human and rodent (Huang et al. Frontiers in Endocrinology 2015 Aug. 17; 6:128). In parallel, biased agonist activity was described for some Relaxin-derived single chain mimetics (Hossain et al. Chem. Sci., 2016, 7, 3805). However based on IUPHAR nomenclature, RXFP1 is a Gs coupled receptor and the main signalling pathway of RXFP1 leads to cAMP (cyclic adenosine monophosphate) accumulation.

Relaxin has been identified first as a pregnancy hormone involved not only in uterus remodelling and embryo implantation but also in the hemodynamic adaptation of pregnant women. This includes decrease vascular resistance, increase in cardiac output and increase GFR, a combination of effect aiming to improve cardiac afterload. These properties have led to the use of recombinant human Relaxin 2 in several clinical trials in the context of acute heart failure.

Beneficial cardiovascular effects of Relaxin, which are attributed to alterations in the renal and systemic vasculature, have also been demonstrated in congestive and acute heart failure patients in preclinical studies and phase II clinical trials. In conscious normotensive and hypertensive male and female rats, acute intravenous and chronic subcutaneous administration of Relaxin increases cardiac output and global arterial compliance and reduces systemic vascular resistance, without affecting mean arterial pressure.

Relaxin has also been shown to reduce mean arterial pressure in rat models of hypertension. The vascular actions of Relaxin extend to modification of passive wall compliance. Chronic subcutaneous Relaxin infusion in rats and mice increases arterial compliance in small renal, mesenteric, uterine and carotid arteries. In addition Relaxin has anti-fibrotic properties in animal model of cardiac and kidney fibrosis.

Thus Relaxin could benefit to patients with chronic heart failure by decreasing after load and relieving heart activity as well as to patients with pulmonary hypertension, with heart failure with reduced or preserved ejection fraction and to patients with fibrotic diseases including systemic sclerosis, idiopathic pulmonary fibrosis and any kidney disease involving fibrosis.

Relaxin-2 is thus clearly of high therapeutic interest.

Nevertheless, H2-Relaxin complex heterodimeric structure makes its chemical synthesis and purification difficult which leads to low yields of final product (Curr. Opin. Chem. Biol. 2014, 22, 47-55).

Accordingly, there is an interest in obtaining stable Relaxin peptides that possess the ability of Relaxin to activate the RXFP1 receptor, and more particularly peptides that retain the biological activity of Relaxin, while being structurally simpler than the native Relaxin.

Peptides with simpler structures could require less complex and more efficient syntheses than H2-Relaxin thereby potentially reducing the cost of treatment linked to H2-Relaxin synthesis.

Furthermore, due to their simpler and smaller structure, such peptides may exhibit an improved uptake compared to native Relaxin, leading to an improved in vivo therapeutic activity.

Several simplified H2-Relaxin analogues have been described in the literature. M. A. Hossain et al. (J. Biol. Chem. (2011), 43, 3755) identified the minimal structure of H2-Relaxin showing that its B-chain could be truncated by up to 6 or 7 amino acids at the N-terminus with minimal loss of potency. The structures described in this publication are double chain Relaxin analogues that are still difficult to synthesize and offer no advantage compared to native H2-Relaxin.

Further attempts were made to simplify Relaxin family peptides. Recently, M. A. Hossain et al. in Chem. Sci. (2016),7, 3805-3819 and WO2015/157829 proposed RXFP1 agonist peptides that comprise only the H2-Relaxin B chain. However, as illustrated in the present text, the peptides of WO2015/157829 present an insufficient capacity to activate the RXFP1 receptor.

There is thus a need for new peptides analogues of the B-chain of Relaxin-2 able to activate the RXFP1 receptor, in particular having an improved ability to activate the RXFP1 receptor.

There is also a need for new modified Relaxin peptides having a simple structure, in particular a simpler structure than the already known Relaxin-peptides, and that possess an improved ability to activate the RXFP1 receptor.

All references cited herein, including patent applications and publications, are incorporated by reference in their entirety.

SUMMARY OF THE INVENTION

The present invention aims to meet the here-above indicated needs.

The inventors indeed provide new modified Relaxin peptides demonstrating a significantly improved capacity to activate the RXFP1 receptor compared to first simplified Relaxin family peptides proposed in the prior art, as demonstrated in the following examples.

As described here-after, several deletions and modifications have been brought by the inventors to the native Relaxin B-chain amino acid sequence, leading to shorter peptides having improved properties compared to the native Relaxin and to the Relaxin peptides already proposed in the prior art. In particular, the enclosed experiments demonstrate that while peptide B7-33 C11.23S (SEQ ID NO: 62) and analogous peptide from WO2015/157829, AcB7-33 C11.23S (SEQ ID NO: 63) and KKKK(AcB7-29 C11.23S) (SEQ ID NO: 64) have a 50% activation concentration ($EC_{50}$) of RXFP1 of 1641 nM, 929 nM and 206 nM respectively, in the cellular assay used to select the peptides of this invention, the $EC_{50}$ values obtained with the peptides according to the invention go from 1.8 nM (SEQ ID NO: 20) up to 251 nM (SEQ ID NO: 42). Moreover, the majority of the tested peptides of the invention have an $EC_{50}$ value lower or equal to 50 nM.

Moreover, while the prior art below suggested that the B-Chain of Relaxin could not be truncated by more than 7 amino-acids (J. Biol. Chem. (2011), 43, 3755; WO2015/157829) without significant reduction in potency, peptides of this invention are truncated by 9 amino-acids at the N-Terminus (Nter) and still show high activity on the RXFP1 receptor.

Compared to RXFP1 agonist peptides of WO2015/157829, peptides of the invention display improved solubility at pH 4.5 or pH 7.5, and improved rat and human plasma or blood stability.

These properties will allow to formulate the peptides of this invention in broad concentration ranges for use as medicament that will retain their in-vivo efficacy for longer period of time, Accordingly, one of the objects of the present invention relates to a peptide having the following formula (I) (SEQ ID NO:65):

$N_{ter}$-X-(E)$_a$-X$_{10}$-E-G-R-E-X$_{15}$-V-R-X$_{18}$-X$_{19}$-I-X$_{21}$-X$_{22}$-E-G-X$_{25}$-S-X$_{27}$-X$_{28}$-X$_{29}$-X$_{30}$-R-(X$_{32}$)$_b$-(X$_{33}$)$_c$-(X$_{34}$)$_d$-NH$_2$-$C_{ter}$ wherein:
$N_{ter}$ represents the N-terminal end of the peptide;
$C_{ter}$ represents the C-terminal end of the peptide;
a, b, c and d independently represent 0 or 1;
X represents hydrogen atom or acetyl group (Ac);
E represents glutamic acid (Glu);
$X_{10}$ represents an amino acid selected from the group consisting of leucine (Leu), 2-amino-isobutyric acid (Aib), α-methyl-leucine (Mel) and Nε-acetyl-lysine (K(Ac));
G represents glycine (Gly);
R represents arginine (Arg);
$X_{15}$ represents an amino acid selected from the group consisting of lysine (Lys), homolysine (Hly), arginine (Arg), homoarginine (Har) and ornithine (Orn);
V represents valine (Val);
$X_{18}$ represents an amino acid selected from the group consisting of alanine (Ala), 2-amino-isobutyric acid (Aib), Nε-acetyl-lysine (K(Ac)), arginine (Arg), leucine (Leu) and glutamine (Gln);
$X_{19}$ represents an amino acid selected from the group consisting of glutamine (Gln), Nε-acetyl-lysine (K(Ac)), alanine (Ala) and 2-amino-isobutyric acid (Aib);
I represents isoleucine (Ile);

$X_{21}$ represents an amino acid selected from the group consisting of alanine (Ala) and 2-amino-isobutyric acid (Aib);

$X_{22}$ represents an amino acid selected from the group consisting of isoleucine (Ile) and 2-amino-isobutyric acid (Aib);

$X_{25}$ represents an amino acid selected from the group consisting of methionine (Met), norleucine (Nle), glutamine (Gln), glutamic acid (Glu) and Nε-acetyl-lysine (K(Ac));

S represents serine (Ser);

$X_{27}$ represents an amino acid selected from the group consisting of threonine (Thr), lysine (Lys), α-methyl-serine (Mse), glutamine (Gln) and arginine (Arg);

$X_{28}$ represents an amino acid selected from the group consisting of tryptophan (Trp), 5-chlorotryptophan (Trp(5-Cl)), 5-fluorotryptophan (Trp(5-F)), 5-methoxytryptophan (Trp(5-OMe)), phenylalanine (Phe), homophenylalanine (Hph), tyrosine (Tyr), 4-fluoro-phenylalanine (Pfp), 1-naphtylalanine (1-Nal) and 2-naphtylalanine (2-Nal);

$X_{29}$ represents an amino acid selected from the group consisting of serine (Ser), alanine (Ala), threonine (Thr), α-methyl-serine (Mse), Nε-acetyl-lysine (K(Ac)) and valine;

$X_{30}$ represents an amino acid selected from the group consisting of lysine (Lys), 2-amino-isobutyric acid (Aib), α-methyl-lysine (Mly), Nε-acetyl-lysine (K(Ac)) and arginine (Arg);

$X_{32}$ represents an amino acid selected from the group consisting of lysine (Lys), arginine (Arg) and Nε-acetyl-lysine (K(Ac));

$X_{33}$ represents an amino acid selected from the group consisting of leucine (Leu), lysine (Lys), Nε-acetyl-lysine (K(Ac)), glutamine (Gln), arginine (Arg) and alanine (Ala); and $X_{34}$ represents an amino acid selected from the group consisting of lysine (Lys) and Nε-acetyl-lysine (K(Ac)); or a salt or a solvate thereof.

A particular embodiment of the invention is a peptide having the formula (I) or a pharmaceutically acceptable salt or a solvate thereof wherein the peptide is able to activate the RXFP1 receptor.

Another embodiment of the present invention is a pharmaceutical composition comprising at least one peptide according to the invention, or a pharmaceutically acceptable salt or a solvate thereof, together with at least one pharmaceutically acceptable carrier.

A further embodiment of the present invention relates to a peptide of the invention, a pharmaceutically acceptable salt or a solvate thereof or a pharmaceutical composition thereof according to the invention, for its use as a medicament.

Accordingly, the present invention further relates to a peptide of the invention, a pharmaceutically acceptable salt or a solvate thereof, or a pharmaceutical composition thereof according to the invention, for its use in the treatment and/or prevention of various diseases or conditions implicating the RXFP1 receptor, more particularly in the treatment and/or prevention of diseases or conditions selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;

the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or the group consisting of renal failures in particular renal dysfunction in cirrhosis, chronic kidney disease and acute kidney injury.

In one embodiment, said disease or condition can be selected from the group consisting of heart and vascular diseases, in particular from the group consisting of acute or chronic heart failure, systolic or diastolic heart failure, coronary artery disease, atherosclerosis, microvascular angina and cardiovascular complication of diabetes.

BRIEF DESCRIPTION OF THE DRAWINGS

The FIGURE is a schema representing a method used for synthesizing the peptides of the invention. This method comprises the assembling of the peptides as C-terminal amides on a CEM Liberty blue microwave peptide synthesizer using standard Fmoc chemistry on a Rink amide AM resin.

DETAILED DESCRIPTION OF THE INVENTION

Definitions

As used herein:

"$X_y$" used in the formulae of the invention with y having different values represents an amino acid as defined in the definition of said formulae. y indicates the position of said amino acid in the native B-chain of Relaxin-2.

For example, $X_{10}$ represents the amino acid in position 10 of the amino acid sequence of the native B-chain of Relaxin-2.

"pharmaceutically acceptable carrier" is intended for a fluid, especially a liquid comprising a peptide of the invention, such that the pharmaceutical composition is physiologically tolerable, i.e. can be administered to the individual body without toxicity or undue discomfort.

a "biologically active" peptide according to the invention is a peptide able to activate the RXFP1 receptor.

An amino acid in the peptides of the invention can each independently be L-amino acids or D-amino acids. In a particular embodiment, amino acids according to the present invention are L-amino acids. In the present text, if no information is indicated regarding the L- or D- form of a given amino acid, then this amino acid is an L-amino acid.

$N_{ter}$ and $C_{ter}$ are conventional labels used to indicate, respectively, the N-terminal end of the peptide and the C-terminal end of the peptide of the invention.

A "peptide" or "Relaxin peptide" according to the invention is a modified Relaxin B chain peptide in accordance with the present invention. In particular, such "peptide" or "Relaxine peptide" means a peptide which is biologically active, i.e. that displays a biological activity typically associated with Relaxin and in particular which is as indicated here-above able to activate the RXFP1 receptor. The level of such Relaxin biological activity displayed by the modified peptides according to the invention may be equivalent or advantageously enhanced when compared with the activity of a naturally occurring or native Relaxin, or even when compared to already disclosed Relaxin peptides different from the one of the present invention.

The term "native" as used in the present text in connection with Relaxin refers to naturally occurring or wild type molecules.

"Preventing" is intended to mean reducing the risk of manifestation of the phenomenon under consideration. This reduction may be total or partial, i.e. results in a degree of risk that is lower than that pre-existing the use according to the invention.

"Treating" is intended to mean reducing or even eliminating the undesirable condition or disease under consideration.

"individual or patient" is intended to mean a human or non-human mammal affected or likely to be affected with a condition considered according to the invention. Said individual is in particular a human being.

Reference to "about" a value or parameter herein includes (and describes) embodiments that are directed to that value or parameter per se. For example, description referring to "about X" includes description of "X."

As used herein, the singular form of the articles "a," "an," and "the" includes plural references unless indicated otherwise.

It is understood that aspects and embodiments of the invention described herein include "comprising," "consisting," and/or "consisting essentially of" aspects and embodiments.

The present inventors have designed new modified peptides.

The inventors have unexpectedly found herein that a shorter and strongly amended peptide according to the invention, i.e. amino acids sequence according to the invention, has a superior biological activity, in particular a superior capacity to activate the RXFP1 receptor in comparison to single B-chain Relaxin known in the art.

Peptides of the Invention

Peptides according to the invention are amended single B-chain Relaxin peptides and are characterized in that they are of formula (I) (SEQ ID NO:65):

$N_{ter}$-X-(E)$_a$-X$_{10}$-E-G-R-E-X$_{15}$-V-R-X$_{18}$-X$_{19}$-I-X$_{21}$-X$_{22}$-E-G-X$_{25}$-S-X$_{27}$-X$_{28}$-X$_{29}$-X$_{30}$-R-(X$_{32}$)$_b$-(X$_{33}$)$_c$-(X$_{34}$)$_d$-NH$_2$-C$_{ter}$ wherein:
$N_{ter}$ represents the N-terminal end of the peptide;
$C_{ter}$ represents the C-terminal end of the peptide;
a, b, c and d independently represent 0 or 1;
X represents hydrogen atom or acetyl group;
E represents glutamic acid;
$X_{10}$ represents an amino acid selected from the group consisting of leucine, 2-amino-isobutyric acid, α-methyl-leucine and Nε-acetyl-lysine;
G represents glycine;
R represents arginine;
$X_{15}$ represents an amino acid selected from the group consisting of lysine, homolysine, arginine, homoarginine and ornithine;
V represents valine;
$X_{18}$ represents an amino acid selected from the group consisting of alanine, 2-amino-isobutyric acid, Nε-acetyl-lysine, arginine, leucine and glutamine;
$X_{19}$ represents an amino acid selected from the group consisting of glutamine, Nε-acetyl-lysine, alanine and 2-amino-isobutyric acid;
I represents isoleucine;
$X_{21}$ represents an amino acid selected from the group consisting of alanine and 2-amino-isobutyric acid;
$X_{22}$ represents an amino acid selected from the group consisting of isoleucine and 2-amino-isobutyric acid;
$X_{25}$ represents an amino acid selected from the group consisting of methionine, norleucine, glutamine, glutamic acid and Nε-acetyl-lysine;
S represents serine;
$X_{27}$ represents an amino acid selected from the group consisting of threonine, lysine, α-methyl-serine, glutamine and arginine;
$X_{28}$ represents an amino acid selected from the group consisting of tryptophan, 5-chlorotryptophan, 5-Fluoro-tryptophan, 5-MethoxyTryptophan, phenylalanine, homophenylalanine, tyrosine, 4-fluoro-phenylalanine, 1-naphtylalanine and 2-naphtylalanine;
$X_{29}$ represents an amino acid selected from the group consisting of serine, alanine, threonine, α-methyl-serine, Nε-acetyl-lysine and valine;
$X_{30}$ represents an amino acid selected from the group consisting of lysine, 2-amino-isobutyric acid, α-methyl-lysine, Nε-acetyl-lysine and arginine;
$X_{32}$ represents an amino acid selected from the group consisting of lysine, arginine and Nε-acetyl-lysine;
$X_{33}$ represents an amino acid selected from the group consisting of leucine, lysine, Nε-acetyl-lysine, glutamine, arginine and alanine; and
$X_{34}$ represents an amino acid selected from the group consisting of lysine and Nε-acetyl-lysine; or a salt or a solvate thereof.

As illustrated, a peptide according to the invention is an amino acid sequence.

On its N-terminal ($N_{ter}$) extremity, a peptide of the invention is substituted with a X group that represents either an hydrogen atom (H) or an acetyl group: $CH_3C(O)$—.

On its C-terminal ($C_{ter}$) extremity, a peptide of the invention is substituted with an —NH$_2$ group.

The present invention also includes salts of the peptides of the above formulae (I) or (Ia), in one embodiment pharmaceutically acceptable salts, for example, salts as acid adduct with inorganic acids such as hydrochloric acid, sulphuric acid, nitric acid, hydrobromic acid, phosphoric acid, perchloric acid, thiocyanic acid and boric acid; or with organic acid such as formic acid, acetic acid, trifluoroacetic acid, propionic acid, glycolic acid, citric acid, tartaric acid, succinic acid, gluconic acid, lactic acid, malonic acid, fumaric acid, anthranilic acid, benzoic acid, cinnamic acid, benzenesulfonic acid, p-toluenesulfonic acid, naphthalenesulfonic acid and sulfanilic acid; and salts with metals such as alkali metal, e.g. sodium, potassium, lithium, zinc, and aluminium.

In one embodiment, the salts of the peptides are pharmaceutically acceptable salts, for example acid adducts with hydrochloric acid, sulphuric acid, phosphoric acid, formic acid, acetic acid, propionic acid, glycolic acid, citric acid, tartaric acid, succinic acid, gluconic acid, lactic acid, malonic acid, fumaric acid, anthranilic acid, benzoic acid, cinnamic acid, benzenesulfonic acid, p-toluenesulfonic acid, naphthalenesulfonic acid and sulfanilic acid; and salts with metals such as alkali metal, e.g. sodium, potassium, lithium and zinc, The present invention also includes solvates, and in one embodiment pharmaceutically acceptable solvates, of the peptides of the above formulae (I) or (Ia).

Solvates mean complexes of the compounds of the invention or salts thereof with solvent molecules, e.g. organic solvent molecules and/or water.

According to an embodiment of the invention, the invention also includes pharmaceutically acceptable salt or solvate of the peptides of the invention.

As illustrated, a peptide according to the invention is an amino acid sequence.

In keeping with standard polypeptide nomenclature (J. Biol. Chem., 243:3552-59 (1969)) abbreviations for a-amino acid residues used in the present invention are as follows:

| One letter code | Three letter code | Amino acid |
|---|---|---|
| A | Ala | Alanine |
| C | Cys | Cysteine |
| D | Asp | Aspartic acid or aspartate |
| E | Glu | Glutamic acid or glutamate |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

For non natural or modified amino acids the following abbreviations are used:

| | |
|---|---|
| Aib | 2-amino-isobutyric acid |
| Har | Homoarginine |
| Hly | Homolysine |
| Hph | Homophenylalanine |
| Nle | Norleucine, 2-amino hexanoic acid |
| K(Ac) | Nε-Acetyl-lysine, 2-amino-4-acetamido-hexanoic acid |
| Mel | α-Methyl-leucine |
| Mly | α-Methyl-lysine |
| Mse | α-Methyl-serine |
| 1-Nal | 1-Naphtylalanine |
| 2-Nal | 2-Naphtylalanine |
| Pfp | 4-Fluoro-phenylalanine |
| Trp(5-Cl) | 5-chlorotryptophan |
| Trp(5-F) | 5-fluorotryptophan |
| Trp(5-OMe) | 5-methoxytryptophan |

In all the formulae according to the invention, where the amino acid sequence is represented by using the above mentioned abbreviations and $X_y$ representations such as $X_{10}$ for example, the left to right orientation is in the conventional direction of amino-terminus to carboxy-terminus.

Accordingly, for example, with $X_{27}$ representing an amino acid selected from the group of threonine, lysine, α-methyl-serine, glutamine and arginine, the N-terminus or amine group of said amino acid is linked to the amino acid represented by S in formula (I) and the C-terminus or carboxyl group of said amino acid is linked to the amino acid represented by $X_{28}$.

When "a" represents 0, the glutamic acid E in position 9 is not present. Accordingly, when "a" represents 0, X is directly linked to $X_{10}$.

Similarly when "b" represents 0, R in position 31, presented in formula (I) between $X_{30}$ and $(X_{32})_b$, is directly linked:
to $(X_{33})_c$ if "c" represents 1;
to $(X_{34})_d$ if "c" represents 0 and "d" represents 1; or
to —NH$_2$ if "c" represents 0 and "d" represents 0;
When c represents 0 and b represents 1, $(X_{32})_b$ is directly linked:
to $(X_{34})_d$ if d represents 1; or
to —NH$_2$ if d represents 0.

When d represents 0 and c represents 1, $(X_{33})_c$ is directly linked to —NH$_2$.

In a particular embodiment, when "b" represents 0, "c" and "d" also represent 0.

In a particular embodiment, when "c" represents 0, "d" also represents 0.

According to a particular embodiment, a peptide according to the invention is of formula (Ia) (SEQ ID NO:66):
N$_{ter}$-X-(E)$_a$-X$_{10}$-E-G-R-E-K-V-R-X$_{18}$-X$_{19}$-I-Aib-X$_{22}$-E-G-X$_{25}$-S-X$_{27}$-X$_{28}$-X$_{29}$-X$_{30}$-R-(X$_{32}$)$_b$-(X$_{33}$)$_c$-(X$_{34}$)$_d$-NH$_2$-C$_{ter}$
wherein:
N$_{ter}$ represents the N-terminal end of the peptide;
C$_{ter}$ represents the C-terminal end of the peptide;
a, b, c and d independently represent 0 or 1;
X represents hydrogen atom or acetyl group;
E represents glutamic acid;
X$_{10}$ represents an amino acid selected from the group consisting of leucine, 2-amino-isobutyric acid and α-methyl-leucine;
G represents glycine;
R represents arginine;
K represents lysine;
V represents valine;
X$_{18}$ represents an amino acid selected from the group consisting of alanine, 2-amino-isobutyric acid, Nε-acetyl-lysine and arginine;
X$_{19}$ represents an amino acid selected from the group consisting of glutamine, Nε-acetyl-lysine, alanine and 2-amino-isobutyric acid;
I represents isoleucine;
Aib represents 2-amino-isobutyric acid;
X$_{22}$ represents an amino acid selected from the group consisting of isoleucine and 2-amino-isobutyric acid;
X$_{25}$ represents an amino acid selected from the group consisting of methionine, norleucine and glutamine;
S represents serine;
X$_{27}$ represents an amino acid selected from the group consisting of threonine, lysine, α-methyl-serine, glutamine and arginine;
X$_{28}$ represents an amino acid selected from the group consisting of tryptophan, 1-naphtylalanine, phenylalanine, tyrosine and 4-fluoro-phenylalanine;
X$_{29}$ represents an amino acid selected from the group consisting of serine, alanine, threonine and α-methyl-serine;
X$_{30}$ represents an amino acid selected from the group consisting of lysine, 2-amino-isobutyric acid, α-methyl-lysine and Nε-acetyl-lysine;
X$_{32}$ represents an amino acid selected from the group consisting of lysine and arginine;
X$_{33}$ represents an amino acid selected from the group consisting of leucine, lysine, Nε-acetyl-lysine, glutamine and arginine; and
X$_{34}$ represents an amino acid selected from the group consisting of lysine and Nε-acetyl-lysine; or a salt or a solvate thereof.

According to a particular embodiment, a peptide according to the invention has an amino acid sequence selected from the group consisting of the amino acid sequences of reference SEQ ID NO: 1 to 59.

In a particular embodiment, a peptide according to the invention is such that X$_{18}$ represents an amino acid selected from the group consisting of alanine and arginine.

In a particular embodiment, a peptide according to the invention is such that X$_{21}$ represents 2-amino-isobutyric acid.

In a particular embodiment, a peptide according to the invention is such that $X_{25}$ represents an amino acid selected from the group consisting of methionine, norleucine and glutamine.

In a particular embodiment, a peptide according to the invention is such that $X_{29}$ represents an amino acid selected from the group consisting of serine and α-methyl-serine.

In a particular embodiment, a peptide according to the invention is such that (i) c represents 0 or (ii) c represents 1 and $X_{33}$ represents an amino acid selected from the group consisting of leucine, lysine, Nε-acetyl-lysine and arginine.

In a particular embodiment, a peptide according to the invention is of formula (Ia) wherein:

$N_{ter}$ represents the N-terminal end of the peptide;
$C_{ter}$ indicates the C-terminal end of the peptide;
X represents hydrogen atom or acetyl group;
a represents 0 or 1;
E represents glutamic acid;
$X_{10}$ represents an amino acid selected from the group consisting of leucine, 2-amino-isobutyric acid and α-methyl-leucine;
G represents glycine;
R represents arginine;
K represents lysine;
V represents valine;
$X_{18}$ represents an amino acid selected from the group consisting of alanine and arginine;
$X_{19}$ represents an amino acid selected from the group consisting of glutamine, Nε-acetyl-lysine, alanine and 2-amino-isobutyric acid;
I represents isoleucine;
Aib represents 2-amino-isobutyric acid;
$X_{22}$ represents an amino acid selected from the group consisting of isoleucine and 2-amino-isobutyric acid;
$X_{25}$ represents an amino acid selected from the group consisting of methionine, norleucine and glutamine;
S represents serine;
$X_{27}$ represents an amino acid selected from the group consisting of threonine, lysine, α-methyl-serine, glutamine and arginine;
$X_{28}$ represents an amino acid selected from the group consisting of tryptophan, 1-naphtylalanine, phenylalanine, tyrosine and 4-fluoro-phenylalanine;
$X_{29}$ represents an amino acid selected from the group consisting of serine and α-methyl-serine;
$X_{30}$ represents an amino acid selected from the group consisting of lysine, 2-amino-isobutyric acid, α-methyl-lysine and Nε-acetyl-lysine;
(i) b represents 0; or (ii) b represents 1 and $X_{32}$ represents an amino acid selected from the group consisting of lysine and arginine;
(i) c represents 0 or (ii) c represents 1 and $X_{33}$ represents an amino acid selected from the group consisting of leucine, lysine, Nε-acetyl-lysine and arginine; and
(i) d represents 0 or (ii) d represents 1 and $X_{34}$ represents an amino acid selected from the group consisting of lysine and Nε-acetyl-lysine;
or a salt or a solvate thereof.

In a particular embodiment of the invention, a peptide of the invention has an amino acid sequence selected from the group consisting of SEQ ID NO: 1-6, 9-17, 19-21, 24-30, 32, 35, 38-41, 46, 48-52 and 54-59. As illustrated in the enclosed examples, the peptides according to this embodiment all have an $EC_{50}$ lower or equal to 50 nM.

In another particular embodiment of the invention, a peptide of the invention has an amino acid sequence selected from the group consisting of SEQ ID NO: 2-5, 13, 16, 17, 19, 20, 25-27, 29, 35, 38, 39, 48, 50-52, 55 and 56. As illustrated in the enclosed examples, the peptides according to this embodiment all have an $EC_{50}$ lower or equal to 20 nM.

In another particular embodiment of the invention, a peptide of the invention has an amino acid sequence selected from the group consisting of SEQ ID NO: 5, 16, 20, 25, 27, 39, 50, 52 and 55. As illustrated in the enclosed examples, the peptides according to this embodiment all have an $EC_{50}$ lower or equal to 10 nM.

In another particular embodiment of the invention, a peptide of the invention has an amino acid sequence selected from the group consisting of SEQ ID NO: 16, 20, 25, 50 and 55. As illustrated in the enclosed examples, the peptides according to this embodiment all have an $EC_{50}$ lower or equal to 5 nM.

A peptide of the invention may be produced by any technique known per se in the art, such as, without limitation, any chemical, biological, genetic or enzymatic technique, either alone or in combination. Knowing the amino acid sequence of the desired sequence, one skilled in the art can readily produce said polypeptides, by standard techniques for production of polypeptides, even if non-natural amino acids are used or according to the methods described herein.

For instance, the peptides of the invention can be synthesized using well-known solid phase method, in particular using a commercially available peptide synthesis apparatus (such as that made by Applied Biosystems, Foster City, Calif., Gyros Protein Technology, Tucson, Ariz. or CEM corporation, Matthews, N.C.) and following the manufacturer's instructions.

Examples of appropriate methods are illustrated in the enclosed examples.

A peptide of the invention can be labelled with at least one detectable molecule or substance, in particular selected from the group consisting of enzymes, prosthetic groups, fluorescent materials, luminescent materials, bioluminescent materials and radioactive materials.

However, it is important that said label does not alter or prevent said peptide from having its biological activity of interest as defined previously, i.e. does not prevent or alter the peptide ability to activate the RXFP1 receptor.

Preferred detectable molecules or substances for the nanomaterial support are those which can be detected externally in a non-invasive manner following in vivo administration.

Detectable molecules or substances are well known to the man skilled in the art.

Such labelled peptide of the invention can be used in a diagnosis and/or imaging method.

A peptide of the invention can also be attached to a moiety, known in the art, to increase in-vivo half-life.

Compositions and Medicaments

The present application also relates to a medicament or a pharmaceutical composition comprising at least one peptide of the invention as described above, or a pharmaceutically acceptable salt or solvate thereof, together with at least one pharmaceutically acceptable carrier.

At least one peptide of the invention is present in a medicament or pharmaceutical composition of the invention as active principle.

A composition or a medicament of the invention is in a form suitable for mammalian administration.

A composition or a medicament of the invention can be administered, for example, orally, parenterally, intravenously, rectally, transdermally, topically or by inhalation. In particular, a composition according to the invention is administered by the intravenous or subcutaneous route, more particularly by the intravenous route.

According to a particular embodiment, the pharmaceutically acceptable carrier of a composition of the invention is suitably selected from the group consisting of an injectable carrier liquid such as sterile water for injection and an aqueous solution such as saline.

A composition or a medicament of the invention can comprise a content of peptides of the invention comprised between 0.01 mg/mL and 30 mg/mL, in particular between 0.3 mg/mL and 3 mg/mL.

A medicament or a pharmaceutical composition of the invention can comprise at least one peptide of the invention as sole active principle or can also comprise at least one other active principles, as long as said other active principle does not prevent the biological activity of the peptide according to the invention.

A pharmaceutical composition or a medicament according to the invention can further comprise at least one antioxidant, dispersant, emulsifier, antifoam, flavouring, preservative, solubilizer and/or colour, as long as this/these additional substances do not prevent the biological properties of the peptides according to the invention.

Sterile compositions of the invention for parenteral administration may in particular be aqueous or non-aqueous solutions, suspensions or emulsions. Solvents or vehicles that can be used include water, propylene glycol, a polyethylene glycol, plant oils, in particular olive oil, injectable organic esters, for example ethyl oleate, or other suitable organic solvents. These compositions may also comprise adjuvants, in particular wetting agents, tonicity agents, emulsifiers, dispersants and stabilisers. The sterilisation may be performed in several ways, for example by aseptic filtration, by incorporating sterilising agents into the composition, by irradiation or by heating. They may also be prepared in the form of sterile solid compositions that may be dissolved at the time of use in sterile water or any other injectable sterile medium.

The compositions for topical administration may be, for example, nasal drops or aerosols.

For subcutaneous, intramuscular or intravenous administration, the peptides of the invention used are converted, if desired with the substances customary for this purpose, such as solubilizers, emulsifiers or other excipients, into a solution, suspension or emulsion. Examples of suitable solvents are: water, physiological saline or alcohols, e.g. ethanol, propanol, glycerol, as well as sugar solutions such as glucose or mannitol solutions, or else a mixture of the various solvents mentioned.

In a particular embodiment, a composition of the invention, a medicament of the invention, or a peptide of the invention is administered to an individual by the parenteral route, and is in particular transdermally, intravenously, subcutaneously or intramuscularly, in particular intravenously or subcutaneously administered.

Methods for preparing parenterally administrable compositions are apparent to those skilled in the art, and are for example described in more detail in Remington's Pharmaceutical Science, 15$^{th}$ ed., Mack Publishing Company, Easton, Pa.

The administration of a composition of the invention or of a peptide of the invention to an individual can be a systemic administration or an administration localized to a tissue, organ and/or site of the individual organism where the presence of, for example a fibrosis, is known, expected or needs to be determined.

Use of the Peptides and Compositions

The present invention relates to a peptide, or its pharmaceutically acceptable salt or solvate thereof, according to the invention for its use as a medicament.

Moreover, the invention also relates to a pharmaceutical composition according to the invention for its use as a medicament.

Furthermore, the present invention relates to a peptide of the invention, its pharmaceutically acceptable salt or solvate thereof, or a pharmaceutical composition of the invention for its use in the treatment and/or prevention of various diseases or conditions implicating the RXFP1 receptor, more particularly in the treatment and/or prevention of diseases or conditions selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;

the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or the group consisting of renal failures in particular renal dysfunction in cirrhosis, chronic kidney disease and acute kidney injury.

In one aspect, such peptide, pharmaceutically acceptable salt or solvate thereof, or composition according to the invention is administered once a day, in particular by the intravenous or subcutaneous route.

The dosage of the peptide, or of its pharmaceutically acceptable salt or solvate thereof, to be administered, and the frequency of administration, depend on the desired effect, the potency and duration of action of the compounds used; additionally also on the nature and severity of the disease or condition to be treated and on the sex, age, weight and individual responsiveness of the mammal to be treated. In general, the doctor will determine the appropriate dosage as a function of the age and weight and all the other factors specific to the individual to be treated.

Also provided herein is a method for preventing and/or treating a disease or condition implicating the RXFP1 receptor comprising administering to an individual in need of said prevention and/or treatment at least one peptide of the invention, its pharmaceutically acceptable salt or solvate thereof, or a pharmaceutical composition of the invention comprising at least one peptide according to the invention or a therapeutically effective amount of least one peptide of the invention, a pharmaceutically acceptable salt or solvate thereof or a pharmaceutical composition of the invention comprising at least one peptide according to the invention.

As previously indicated, said disease or condition is in particular selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia;

the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or the group consisting of renal failures in particular renal dysfunction in cirrhosis, chronic kidney disease and acute kidney injury.

In particular, said disease or condition is selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia; and the group consisting of heart and vascular diseases, in particular from the group consisting of acute or chronic heart failure, systolic or diastolic heart failure, coronary artery disease, atherosclerosis, microvascular angina and cardiovascular complication of diabetes.

It is further described the use of at least one peptide according to the invention, its pharmaceutically acceptable salt or solvate thereof, or of a pharmaceutical composition according to the invention for treating and/or preventinf a disease or condition selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia; and/or the group consisting of heart and vascular diseases, in particular from the group consisting of acute or chronic heart failure, systolic or diastolic heart failure, coronary artery disease, atherosclerosis, microvascular angina and cardiovascular complication of diabetes; and/or the group consisting of renal failures in particular renal dysfunction in cirrhosis, chronic kidney disease and acute kidney injury;

and in particular for treating and/or preventing a disease or condition selected from:

the group consisting of fibrosis; fibrotic diseases, in particular systemic sclerosis, scleroderma and fibromyalgia; idiopathic pulmonary fibrosis; kidney diseases involving fibrosis; pulmonary hypertension and preeclampsia; and the group consisting of heart and vascular diseases, in particular from the group consisting of acute or chronic heart failure, systolic or diastolic heart failure, coronary artery disease, atherosclerosis, microvascular angina and cardiovascular complication of diabetes.

The present invention is illustrated by the following examples, given purely for illustrative purposes.

EXAMPLES

Example 1: Synthesis of the Peptides of the Invention

Material Used

Various rink amide type resins were used for the synthesis of C-terminal amides peptides of the invention:

4-(2',4'-Dimethoxyphenyl-Fmoc-aminomethyl)phenoxy resin, sold by Chem-Impex; or 4-(2',4'-Dimethoxyphenyl-Fmoc-aminomethyl)phenoxy acetamido methyl resin, sold by Millipore Merck;

They were loaded in the range of 0.2 to 0.4 mmol/g.

Fmoc (fluorenylmethyloxycarbonyl) protected natural amino acids were purchased from different sources, i.e. Protein Technologies Inc., Merck Biosciences, Novabiochem, Iris Biotech, Bachem, Chem-Impex International or MATRIX Innovation.

The following standard amino acids were used throughout the syntheses: Fmoc-L-Ala-OH, Fmoc-L-Arg(Pbf)-OH, Fmoc-L-Gln(Trt)-OH, Fmoc-L-Glu(OtBu)-OH, Fmoc-Gly-OH, Fmoc-L-Ile-OH, Fmoc-L-Leu-OH, Fmoc-L-Lys(Boc)-OH, Fmoc-L-Met-OH, Fmoc-L-Phe-OH, Fmoc-L-Ser(tBu)-OH, Fmoc-L-Thr(tBu)-OH, Fmoc-L-Trp(Boc)-OH, Fmoc-L-Tyr(tBu)-OH and Fmoc-L-Val-OH.

In addition, the following special amino acids were purchased from the same suppliers as above: Fmoc-Aib-OH, Fmoc-Hly(Boc)-OH, Fmoc-Har(Pbf)-OH, Fmoc-Hph-OH, Fmoc-L-Lys(Ac)-OH, Fmoc-Aib-OH, Fmoc-L-α-Me-Ser(tBu)-OH, Fmoc-L-α-Me-Lys(Boc)-OH, Fmoc-L-α-Me-Leu-OH Fmoc-L-Nle-OH, Fmoc-L-1-Nal-OH, Fmoc-L-2-Nal-OH, Fmoc-Orn(Boc)-OH, Fmoc-Trp(5-Cl)-OH, Fmoc-Trp(5-F)-OH and Fmoc-Trp(5-OMe)-OH.

The following additional abbreviations were used:

| | |
|---|---|
| Ac | Acetyl |
| cAMP | Cyclic adenosine monophosphate |
| Boc | Tert-Butyloxycarbonyl |
| tBu | Tert-Butyl |
| DCM | Dichloromethane |
| DIC | N,N'-Diisopropylcarbodiimide |
| DIEA | N,N-Diisopropyl ethylamine |
| DMF | N,N-Dimethylformamide |
| DODT | 2,2'-(Ethylenedioxy)diethanethiol |
| EDT | 1,2-ethanedithiol |
| Fmoc | Fluorenylmethyloxycarbonyl |
| TFA | Trifluoroacetic acid |
| TIS, TIPS | Tri-isopropyl Silane |
| HATU | (2-(7-Aza-1H-benzotriazol-1-yl)-N,N,N',N'-tetramethylaminium hexafluorophosphate) |
| HPLC | High Performance Liquid Chromatography |
| HTRF | HTRF Homogenous Time Resolved Fluorescence |
| LC/MS | Liquid Chromatography/Mass Spectrometry |
| NMP | 1-methylpyrrolidin-2-one |
| Oxyma | Ethyl 2-cyano-2-(hydroximino)acetate (oxyma pure ™) |
| RP-HPLC | Reversed-phase high performance liquid chromatography |
| RT | Retention Time |
| TFA | Trifluoroacetic acid |
| Trt | Trityl, Triphenylmethyl |
| UV | ultraviolet |
| UPLC | Ultra high Performance Chromatography |

1.A. First Method Used for Synthesizing the Peptides of the Invention

Several of the peptides according to the invention of sequence SEQ ID NO: 1-59 have been synthesized on the basis of the following method.

Said peptides were assembled as C-terminal amides on a CEM Liberty blue microwave peptide synthesizer using standard Fmoc chemistry on a Rink amide AM resin, on the basis of the schema represented in the FIGURE.

The standard protocol was used for 0.1 to 0.2 mmol scale. As indicated, the entire synthesis was run in N,N-Dimethylformamide (DMF) as solvent.

Standard heating protocol: irradiation at 170 watts, 75° C., 15 sec. then irradiation at 30 watts, 90° C., 120 sec.

Deprotection was performed with 20% v/v piperidine in DMF, followed by 3 DMF washing steps.

Heating protocol for deprotection: irradiation at 170 watts, 75° C., 15 sec. then irradiation at 30 watts, 90° C., 50 sec.

Amino acid couplings were performed using 5 eq. of Fmoc-AA as 0.2 M solutions in DMF using 5 eq. N,N'-Diisopropylcarbodiimide (DIC) 0.5M and 5 eq. Oxyma (Ethyl 2-cyano-2-(hydroximino)acetate (oxyma Pure™)) 1M as coupling reagents.

For better final yield, each amino-acid required double couplings at 90° C. for 120 seconds. For 2-aminoisobutyric acid at position $X_{21}$ of the formula (I) according to the invention, a triple coupling at 90° C. for 2 minutes was used.

At the end of the synthesis, Fmoc deprotection was performed manually with 20% V/V piperidine in DMF two times 30 minutes.

Acetylation was performed at N-terminus for some peptides of the invention by treatment with 5-10 eq. of acetic anhydride and 5-10 eq. N,N-Diisopropyl ethylamine (DIEA) in DMF for 15 to 90 minutes. Then, the resin containing the fully protected peptide was washed with dichloromethane (DCM)/DMF/DCM, three times each, and then dried under vacuum.

1.B. Second Method Used for Synthesizing the Peptides of the Invention

Several of the peptides according to the invention of sequence SEQ ID NO: 1-59 have been synthesized on the basis of the following method.

The same synthesis schema as indicated in point 1A was used, but on a Symphony peptide synthesizer (Gyros Protein Technology) using Fmoc chemistry on a Rink amide AM resin.

The standard protocol for 0.15 mmol scale was used. The entire synthesis was run at room temperature in DMF as solvent, using as activators (2-(7-Aza-1H-benzotriazol-1-yl)-N,N,N',N'-tetramethylaminium hexafluorophosphate) (HATU) 0.3M/DIEA 1.2M.

Each amino acid was coupled using 45 minutes double coupling protocol, with the exception of 2-aminoisobutyric acid at position $X_{21}$ of the formula (I) according to the invention and isoleucine at position 20 (i.e. the isoleucine comprised between $X_{19}$ and $X_{21}$ of formula (I) according to the invention), for which a 45 minutes triple coupling was required for completion.

In some instances, it could be advantageous to use mixtures of solvent, such as DCM/DMF or DCM/N-methylpyrrolidone (NMP) 1:1 mixtures which are known to accelerate and/or improve the yield of the coupling step.

At the end of the synthesis, Fmoc deprotection with 20% V/V piperidine/DMF was performed manually for each peptide as above.

Acetylation was performed at N-terminus for some peptides of the invention by treatment with 5-10 eq. of acetic anhydride and 5-10 eq. DIEA in DMF for 15 to 90 minutes.

Then the resin containing the fully protected peptide was washed with DCM/DMF/DCM, three times each, and dried under vacuum.

1.C. Peptide-Resin Cleavage

Upon completion of solid phase synthesis, the peptide was cleaved from the solid support by treatment with cleavage reagent B: TFA/phenol/$H_2O$/TIPS (Tri-isopropylsilane) (87.5%/5%/5%/2.5%/25 ml) for 3 h.

In certain instances, addition of a dithiol such as 1,2-ethane dithiol or DODT (2,2'-(ethylenedioxy)diethanethiol) may be advantageous (e.g. reagent K). The TFA solution containing the peptide was filtered and concentrated under reduced pressure at T<30° C.

The desired product was precipitated with ice-cold MTBE (methyl tert-butyl ether) or diethyl ether and centrifuged at 3000 rpm for 30 min. The centrifuged pellet was then washed with ice-cold diethyl ether and centrifuged. This process was repeated three times.

In some instances it may be necessary to process the crude peptide to remove undesired by-products such as TFA esters, $CO_2$ adduct on indole nitrogen of tryptophan (carbamic acid) and 2-t-butyl-sulfanylethyl adduct on Methionine residues.

To remove $CO_2$ adduct on indole nitrogen of tryptophan, the crude peptide was taken up in water containing 10-20% $CH_3CN$, 5 mg/ml and lyophilized.

To remove 2-t-butyl-sulfanylethyl adduct on Met, the crude peptide was dissolved (2 mg/ml) in a solution of $H_2O/CH_3CN$ (50:50 v/v) containing 0.1% formic acid.

The mixture was gently stirred at 37° overnight.

To remove TFA esters, the crude peptide was dissolved (2 mg/ml) in a solution of $H_2O/CH_3CN$ (50:50 v/v) containing 0.1% formic acid. The mixture was gently stirred at 37° for 1-4 h.

In both cases, the crude peptide solution thus obtained was partially concentrated under reduced pressure and at T<30° C. and lyophilized.

1.D. Purification Step

Following any of the above method indicated for synthesizing a peptide of the invention, said peptide was purified before being used in physico-chemical and biological assays.

80 mg of crude peptide were dissolved in 1.5 mL DMSO and purified by Reverse Phase High Pressure Liquid Chromatography (RP-HPLC). The RP-HPLC is described in the following part 1.E.

A GX271 Liquid Handler, 333/334 pumps, and UV/VIS 151 Gilson system was used.

Two different systems were used in order to purify said peptides:

System A

Column Reprosil C4 μm 120A. 250×40 mm;
Solution A: 0.1% Trifluoroacetic acid (TFA) in $H_2O$;
Solution B: 0.1% TFA in acetonitrile;
Gradient: 30% B for 5 min; 30% B to 50% B in 20 min;
Flow rate: 60 ml/min.

System B

Column Waters CSH C18 μm 250×50 mm, or Waters Sunfire C18 10 μM 250×50 mm;
Solution A=0.1% TFA in water;
Solution B=0.1% TFA in acetonitrile;
Gradient: from 1% B to 18% B in 5 min; from 18% B to 28% B in 10 min; 28% B for 15 min; from 28% B to 48% B in 10 min; then column wash from 48% B to 90% B in 10 min;
Flow rate: 150 ml/min.

The peptide of interest was eluted in the 35-40 min time window.

The gradient was slightly adjusted according to the polarity of each peptide as characterized by its retention time on an analytical UPLC System.

The fractions containing the pure peptide were then partially concentrated under reduced pressure at T<35° C. and lyophilized until constant weight.

For certain uses (e.g. in-vivo testing), it was advantageous to exchange the TFA salt to the acetate salt. Three corresponding methods were used and are described in the following part 1.E.

1.E. Acetate Exchange

(i) Acetate Exchange with TOYOPEARL® DEAE 650 C (Tosoh Corporation)

The ion exchange was performed using a TOYOPEARL® DEAE 650 C grade resin (a weak anion exchange resin).

120 ml of resin was washed sequentially with 15 volumes of NaOH 1M, 5 volumes of $H_2O$, 5 volumes of acetic acid 1.6M, 5 volumes of acetic acid 0.16M and finally 5 volumes of $H_2O$.

41.8 mg of peptide was then dissolved in 20 ml of distilled water, downloaded to the resin and gently mixed for 2 h.

Finally, the peptide was collected by elution and washed with water and lyophilized.

Peptide Recovery: 35 mg (as acetate salt by F19 NMR (400 MHz) ns 1028).

(ii) Acetate Exchange with Sepharose HiTrap Q HP Column (Strong Anionic Exchange Column)

In this second method, the ion exchange was performed using a HiTrap Q HP.

The column (5ml bed volume) was connected to a peristaltic pump set at 48 (4.5 ml/min) and before loading the peptide it was washed with 50 ml (10 column volumes) of $H_2O$, 100 ml (20 column volumes) of a 1M solution of sodium acetate, 150 ml (30 column volumes) of $H_2O$ and with 50 ml (10 column volumes) of 0.16 M solution of acetic acid.

The pure peptide was dissolved in a 0.16 M acetic acid solution at 2 mg/ml, slowly loaded on the column and eluted at 4.5 ml/min.

The collected solution was freeze-dried.

The effectiveness of the ion exchange was attested by F19 NMR (400 MHz) ns 1028.

(iii) Acetate Exchange Using RP-HPLC

The material used was the following:

Column Waters CSH C18 5 µm 250×50 mm, or Waters Sunfire C18 10 µM 250×50 mm;

Solution A=1% Acetic acid in water;

Solution B=1% Acetic acid in acetonitrile;

After, previously purified peptide injection on the column, a 10 mM ammonium acetate solution in water was run for 10 minutes. Then the solvent system was switched to the following AB gradient:

Gradient: from 1% B to 7% B for 5 min; from 7% B to 17% B in 10 min; 17% B for 15 min; from 17% B to 27% B in 10 min; then column wash from 27% B to 95% B in 10 min.

Flow rate: 150 ml/min.

The peptide of interest was eluted in the 35-40 min time windows. The gradient was slightly adjusted according to the polarity of each peptide as characterized by its retention time on an analytical UPLC System.

The fractions containing the pure peptide were then partially concentrated under reduced pressure at T<35° C. and lyophilized until constant weight.

The effectiveness of the ion exchange was attested by F19 NMR (400 MHz) ns 1028.

Example 2: Illustrative Synthesis of Specific Peptides of the Invention

2.A. Synthesis of Peptide Having the SEQ ID NO: 3

287 mg of Rink Amide AM LL resin (NovaBiochem cat#8.55 120) corresponding to approximately 0.11 mmol of active Fmoc amino functions were swelled in 10 ml of 1:1 DCM/DMF mixture.

The resin was placed in the CEM Liberty Blue reactor and the programmed sequence was run as described above.

Then the resin was transferred to a 20 ml syringe equipped with a filter and washed with 3×10 ml DCM (Dichloromethane) and dried under vacuum.

The resin was swelled in 5 ml DMF, DIEA (85.46 µl, 500 µmol) and acetic anhydride (47.74 µl, 500 µmol) were added and the syringe was agitated on an orbital table for 1.5 h.

The solvent was filtered off and the resin was washed with DMF (10 ml) and 3×10 ml DCM and dried under vacuum.

The resin weighted 720 mg.

A solution of phenol (500 mg), thioanisole (0.5 ml) water (0.5 ml) and 2,2'-(ethylenedioxy)diethanethiol (DODT) (0.25 ml) in TFA (QSP 10 ml) was added to the resin. The suspension was degased by bubbling nitrogen for 10 min and agitated on an orbital table for 2 h.

The resin was filtered off, the solution was then transferred to a 250 ml round bottom flask, and the suspension was washed with 2×5 ml TFA. The mixture was partially concentrated under vacuum at T<30° C. and the peptide was precipitated by the addition of 100 ml cold diethyl ether. The solid was collected by centrifugation (1000 rpm) and washed three times with cold diethyl ether.

After drying under vacuum 250 mg of crude peptide was obtained.

Purification was performed using the purification condition indicated here-above and the fractions containing pure desired peptide were lyophilized.

The peptide as trifluoro acetate salt was obtained as a white solid.

m=73 mg (21%);

UPLC/MS:

Retention Time (RT): 3.34 min. (Analytical condition A); purity 98% (UV);

observed mass m/z (ion type): 1384.2 (M+2H); 923.5 (M+3H); 692.8 (M+4H).

2.B. Synthesis of Peptide Having the SEQ ID NO: 5

Following the procedure used in example 2.A., from 287 mg of Rink Amide AM LL resin (NovaBiochem cat #8.55 120), 780 mg of peptide loaded resin was obtained.

The cleavage from the resin was performed as in example 2.A. but after the diethyl ether washings, the crude peptide was solubilized in 20 ml 30% $CH_3CN$/water and lyophilized.

250 mg of crude peptide were obtained.

Purification was performed using purification condition B and the fractions containing pure desired peptide were lyophilized. The peptide as trifluoro acetate salt was obtained as a white solid.

m=70 mg (20%);
UPLC/MS:
RT: 3.20 min (Analytical condition H);
purity 97% (UV);
observed mass m/z (ion type): 1426.9 (M+2H); 951.3 (M+3H); 713.9 (M+4H).

2.C. Synthesis of Peptide Having the SEQ ID NO: 52

Following the procedure used in example 2.A., from 250 mg of Rink Amide AM LL resin (NovaBiochem cat #8.55 120), 500 mg of peptide loaded resin was obtained after N-terminus acetylation.

The cleavage of the peptide from the resin was performed using a solution phenol (500 mg), water (0.5 ml) and TIPS (Tri-isopropyl silane) (0.25 ml) in TFA (QSP 10 ml) for 2 hours at room temperature.

The resin was filtered off, the solution was then transferred to a 250 ml round bottom flask, the suspension was washed with 2×5 ml TFA. The mixture was partially concentrated under vacuum at T<30° C. and the peptide was precipitated by the addition of 100 ml cold diethyl ether.

The solid was collected by centrifugation (1000 rpm) and washed three times with cold diethyl ether. 140 mg of crude peptide were obtained.

Purification was performed using purification condition B and the fractions containing pure desired peptide were lyophilized. The peptide as trifluoro acetate salt was obtained as a white solid.
m=44 mg (12%);
UPLC/MS:
RT: 3.32 min (Analytical condition A);
purity 96% (UV);
observed mass m/z (ion type): 950.8 (M+3H); 13.4 (M+4H).

2.D. Synthesis of Peptide Having the SEQ ID NO: 53

Following the procedure used in example 2.C., from 250 mg of Rink Amide AM LL resin (NovaBiochem cat #8.55 120), 169 mg of crude peptide were obtained.

Purification was performed using purification condition B and the fractions containing pure desired peptide were lyophilized.

The peptide as trifluoro acetate salt was obtained as a white solid.
m=54 mg (15%);
RT: 3.15 min (Analytical condition A) purity 97% (UV);
observed mass m/z (ion type); 915.5 (M+3H); 687.0 (M+4H).

2.E. Synthesis of Peptide Having the SEQ ID NO: 54

Following the procedure used in example 2.C., from 250 mg of Rink Amide AM LL resin (NovaBiochem cat #8.55 120), 200 mg of crude peptide were obtained.

Purification was performed using purification condition B and the fractions containing pure desired peptide were lyophilized.

The peptide as trifluoro acetate salt was obtained as a white solid.
m=50 mg (14%);
RT: 2.93 min (Analytical condition A) purity 93% (UV);
observed mass m/z (ion type): 1392.3 (M+4H); 928.1 (M+3H); 696.4 (M+4H).

2.F. Results

The results obtained with all the peptides of the invention of SEQ ID NO: 1-59 are indicated in the following Table 1.

TABLE 1

| SEQ ID NO | UPLC Ret. Time Min. (Conditions) | Observed mass Ion type | | | | Mono isotopic mass |
|---|---|---|---|---|---|---|
| | | M + 5H | M + 4H | M + 3H | M + 2H | |
| 1 | 2.44 (I) | 577.7 | 722.4 | 962.6 | 1442.7 | 2882.6 |
| 2 | 2.26 (I) | 571.9 | 714.9 | 953.3 | | 2854.6 |
| 3 | 3.34 (A) | 554.6 | 692.6 | 923.5 | 1384.2 | 2766.5 |
| 4 | 2.47 (J) | 558.2 | 697.2 | 929.1 | 1393.9 | 2784.5 |
| 5 | 3.20 (H) | 571.2 | 713.9 | 951.3 | 1426.9 | 2850.6 |
| 6 | 2.26 (I) | 569.7 | 711.8 | 948.7 | 1422.7 | 2840.6 |
| 7 | 2.59 (I) | 580.7 | 725.7 | 967.4 | 1451.0 | 2896.6 |
| 8 | 2.60 (I) | 574.4 | 717.9 | 956.8 | 1434.8 | 2864.6 |
| 9 | 2.62 (I) | 580.0 | 724.8 | 966.5 | 1449.5 | 2893.6 |
| 10 | 3.01 (F) | 567.0 | 708.8 | 944.4 | 1416.3 | 2827.5 |
| 11 | 3.18 (B) | 566.7 | 708.3 | 943.6 | 1415.7 | 2826.5 |
| 12 | 3.79 (L) | 558.5 | 697.5 | 930.1 | 1393.9 | 2786.1 |
| 13 | 3.63 (E) | 563.5 | 704.1 | 938.6 | 1407.3 | 2809.6 |
| 14 | 2.66 (I) | 571.3 | 713.5 | 950.7 | 1426.0 | 2847.6 |
| 15 | 2.95 (I) | 565.3 | 706.0 | 941.9 | 1412.9 | 2820.6 |
| 16 | 2.48 (I) | 555.2 | 693.9 | 925.0 | 1387.1 | 2770.5 |
| 17 | 3.03 (I) | | 678.5 | 905.2 | 1355.8 | 2709.5 |
| 18 | 2.68 (I) | 538.3 | 672.4 | 896.1 | 1343.7 | 2683.4 |
| 19 | 3.85 (E) | 554.8 | 693.3 | 924 | 1385.7 | 2766.5 |
| 20 | 2.72 (I) | 557.8 | 6976.7 | 928.9 | 1393.0 | 2780.6 |
| 21 | 2.8 (I) | 563.1 | 703.3 | 937.4 | 1405.6 | 2808.5 |
| 22 | 2.7 (I) | 551.4 | 689.3 | 918.4 | 1377.7 | 2750.5 |
| 23 | 3.02 (H) | 557.7 | 696.6 | 928.5 | 1392.2 | 2780.5 |
| 24 | 3.2 (H) | 563.1 | 703.7 | 937.2 | 1405.4 | 2808.6 |
| 25 | 3.2 (H) | 580.0 | 724.6 | 965.6 | 1448.1 | 2893.6 |
| 26 | 3.39 (H) | 588.8 | 735.2 | 979.9 | 1469.3 | 2935.6 |
| 27 | 3.46 (G) | 571.6 | 714.3 | 951.9 | 1427.6 | 2850.6 |
| 28 | 3.77 (G) | 579.7 | 724.8 | 965.9 | 1448.7 | 2892.6 |
| 29 | 3.0 (I) | 573.5 | 716.4 | 955.6 | 1433.5 | 2861.6 |
| 30 | 4.57 (C) | | 717.9 | 955.9 | 1434.1 | 2864.6 |
| 31 | 3.26 (H) | 562.8 | 703.5 | 937.8 | 1406.1 | 2808.5 |
| 32 | 2.82 (K) | 559.9 | 699.6 | 932.6 | 1398.5 | 2793.5 |
| 33 | 3.07 (H) | 574.5 | 719.7 | 956.8 | 1435.0 | 2865.6 |
| 34 | 3.33 (H) | 565.6 | 706.6 | 942.2 | 1413.5 | 2822.6 |
| 35 | 3.13 (D) | 557.7 | 696.8 | 928.8 | 1392.5 | 2781.5 |
| 36 | 2.73 (I) | | 649.6 | 865.6 | 1298.0 | 2591.4 |
| 37 | 3.0 (I) | 642.5 | 642.5 | 856.4 | 1284.2 | 2564.4 |
| 38 | 2.55 (G) | | 651.4 | 868.1 | 1301.2 | 2598.4 |
| 39 | 2.99 (H) | | 644.1 | 858.5 | 1287.4 | 2571.3 |
| 40 | 2.82 (I) | | 644.6 | 858.9 | 1288.1 | 2571.3 |
| 41 | 2.93 (I) | | 633.5 | 844.3 | 1266.6 | 2528.3 |
| 42 | 2.98 (I) | | 637.2 | 8490 | 1273.0 | 2542.3 |
| 43 | 3.12 (I) | 623.3 | 623.2 | 830.2 | 1244.5 | 2485.3 |
| 44 | 2.77 (I) | | 660.7 | 880.7 | 1320.8 | 2638.4 |
| 45 | 2.63 (I) | | 665.5 | 886.8 | 1329.5 | 2656.4 |
| 46 | 3.72 (E) | | 640.4 | 853.6 | 1279.8 | 2555.3 |
| 47 | 3.5 (G) | | 671.5 | 895.1 | 1342.2 | 2680.5 |
| 48 | 2.95 (G) | 568.7 | 710.8 | 947.2 | 1420.8 | 2838.5 |
| 49 | 3.10 (A) | 571.5 | 714.1 | 951.8 | 1426.8 | 2851.6 |
| 50 | 3.32 (A) | | 706.6 | 941.8 | 1412.7 | 2849.5 |
| 51 | 3.33 (A) | 546.7 | 682.8 | 910.1 | 1364.7 | 2727.5 |
| 52 | 3.32 (A) | | 713.4 | 950.8 | | 2849.5 |
| 53 | 3.15 (A) | | 687.0 | 915.5 | | 2743.5 |
| 54 | 2.93 (A) | | 696.4 | 928.1 | 1392.3 | 2781.5 |
| 55 | 3.24 (A) | 576.5 | 720.3 | 960.2 | | 2877.6 |
| 56 | 3.21 (H) | | 717.3 | 955.9 | 1433.3 | 2864.6 |
| 57 | 2.95 (A) | 549.5 | 686.6 | 915.1 | | 2742.5 |
| 58 | 2.8 (A) | 552.8 | 690.6 | 920.4 | | 2758.5 |
| 59 | 3.0 (A) | 553.1 | 691.1 | 921.1 | | 2760.5 |

Condition A was the Following:
Column: Acquity Peptide CSH, C18, 130 Å, 2.1×100 mm, 1.7 um;
Column Temperature: 50° C.; Flow=0.6 ml/min;
Solvent A: 0.1% TFA in H$_2$O;

Solvent B: 0.1% TFA in CH$_3$CN;
Gradient: from 0 to 1 min B=2%, from 1 to 7 min B=2% to 70%, from 7 to 8 min B=70% to 100%;
UV detector: wavelength: 220 nm; MS acquisition: ESI+200 to 3000 uma.
Condition B was the Following:
Column: ACQUITY BEH C4, 130 Å, 2.1×50 mm, 1.7 µm;
Column temperature 45° C.; Flow rate: 0.4 ml/min; -Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=10%, from 1 to 5 min B=10% to 50%, from 5 to 6 min B=50% to 90%.
Condition C was the Following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=15%, from 1 to 5 min B=15% to 35%, from 5 to 6 min B=35% to 80%.
Condition D was the Following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=15%, from 1 to 5 min B=15% to 35%, from 5 to 6 min B=35% to 90%.
Condition E was the Following:
Column: ACQUITY BEH C4, 130 Å, 2.1×50 mm, 1.7 µm;
Column temperature 45° C.; Flow rate: 0.4 ml/min; -Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=15%, from 1 to 5 min B=15% to 40%, from 5 to 6 min B=40% to 90%.
Condition F was the Following:
Column: ACQUITY BEH C4, 130 Å, 2.1×50 mm, 1.7 µm;
Column temperature 45° C.; Flow rate: 0.4 ml/min; -Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=15%, from 1 to 5 min B=15% to 50%, from 5 to 6 min B=50% to 90%.
Condition G was the Following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=20%, from 1 to 5 min B=20% to 40%, from 5 to 6 min B=40% to 80%.
Condition H was the Following:
Column: ACQUITY BEH C4, 130 Å, 2.1×50 mm, 1.7 µm;
Column temperature 45° C.; Flow rate: 0.4 ml/min; -Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=20%, from 1 to 5 min B=20% to 40%, from 5 to 6 min B=40% to 90%.
Condition I was the Following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=20%, from 1 to 5 min B=20% to 60%, from 5 to 6 min B=60% to 80%.
Condition J was the Following:
Column: ACQUITY BEH C4, 130 Å, 2.1×50 mm, 1.7 µm;
Column temperature 45° C.; Flow rate: 0.4 ml/min; -Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=20%, from 1 to 5 min B=20% to 60%, from 5 to 6 min B=60% to 90%.
Condition K was the Following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=25%, from 1 to 5 min B=25% to 45%, from 5 to 6 min B=45% to 90%.
Condition L was the Following:
Column: ACQUITY BEH C4, 130 Å, 2.1×50 mm, 1.7 µm;
Column temperature 45° C.; Flow rate: 0.4 ml/min;
Solvent A: 0.1% TFA in H$_2$O;
Solvent B: 0.1% TFA in CH$_3$CN;
UV detector: wavelength: 214 nm; MS acquisition: ESI+200 to 3000 uma;
Elution system: from 0 to 1 min B=5%, from 1 to 5 min B=5% to 40%, from 5 to 6 min B=40% to 80%.

Example 3: In Vitro Analysis of Peptides of the Invention on the RXFP1 Receptor (OVCAR5 cAMP Assay)

A. Method

OVCAR5 cells expressing endogenous RXFP1 were used to test RXP1 agonist properties of peptides of the invention, and in particular of the peptides of sequence SEQ ID NO: 1-59.

Since RXFP1 is a Gs coupled GPCR, cAMP was used as readout of RXFP1 activation.

Isobutyl Methyl Xanthine (IBMX) was used to inhibit phosphodiesterase activity facilitating cAMP measurements. HTRF (Homogenous Time Resolved Fluorescence) technology was used to detect cAMP due to its great sensitivity.

In summary, OVCAR5 were grown in regular medium (RPMI) containing 10% fetal calf serum (FCS) and 1% antibiotics (penicillin/streptomycin).

Before the experiments, cells were detached with accutase and incubated for 40 minutes at 37° C. with 1 mM (3-isobutyl-1-methylxanthine) IBMX.

Cells were then distributed in 384 black well plates containing increasing concentrations of the different peptides in a fix volume of medium (without FCS).

After an incubation of 30 min at 37° C. in a humid incubator in 5% $CO_2$, the reaction was stopped by adding a fixed volume of a solution containing a lysis buffer and cAMP-D2 (cAMP labeled with the dye d2) and the anti cAMP antibody linked to Europium and used for cAMP detection.

Readouts of the experiments were performed on a fluorimeter allowing HTRF measurement. Activation curves were generated by plotting the intracellular value of cAMP versus log 10 of the compound concentration.

The 50% activation concentration ($EC_{50}$) was calculated by nonlinear regression using the sigmoidal dose-response (variable slope) equation with Prism 5 software.

Emax % was determined as the maximal intracellular value of cAMP for test compound (upper limit of cAMP vs concentration curve) divided by the maximal intracellular value of cAMP for H2-relaxin determined in the same test occasion multiplied by 100:

$$Emax\ \% = 100 \times [cAMP_{test\ cpd}]/[CAMP_{H2-Rlx}]$$

B. Results

In each test occasion H2-Relaxin was tested as a reference compound at the same time as the test compounds. Assay was considered valid if H2-Relaxin $EC_{50}$ was in the 0.1 to 0.3 nM range.

The results obtained are represented in the following Table 2.

TABLE 2

| SEQ ID NO | cAMP assay in OVCAR 5 cells | |
|---|---|---|
| | $EC_{50}$ (nM) | Emax |
| 1 | 42.9 | 91% |
| 2 | 14.4 | 99% |
| 3 | 12.0 | 97% |
| 4 | 14.1 | 99% |
| 5 | 7.4 | 98% |
| 6 | 46.3 | 97% |
| 7 | 56.6 | 101% |
| 8 | 60.0 | 103% |
| 9 | 37.6 | 100% |
| 10 | 22.9 | 103% |
| 11 | 44.8 | 102% |
| 12 | 28.2 | 99% |
| 13 | 19.2 | 97% |
| 14 | 32.8 | 106% |
| 15 | 24.4 | 104% |
| 16 | 4.6 | 101% |
| 17 | 11.6 | 90% |
| 18 | 52.1 | 104% |
| 19 | 18.2 | 97% |
| 20 | 1.8 | 97% |
| 21 | 32.8 | 96% |
| 22 | 57.1 | 102% |
| 23 | 127.6 | 95% |
| 24 | 47.9 | 92% |
| 25 | 4.2 | 100% |
| 26 | 14.5 | 100% |
| 27 | 9.5 | 95% |
| 28 | 22.5 | 92% |
| 29 | 13.8 | 98% |
| 30 | 41.6 | 93% |
| 31 | 51.7 | 96% |
| 32 | 38.6 | 95% |
| 33 | 86.3 | 105% |
| 34 | 68.7 | 96% |
| 35 | 15.8 | 98% |
| 36 | 126.9 | 103% |
| 37 | 52.4 | 104% |

TABLE 2-continued

| SEQ ID NO | cAMP assay in OVCAR 5 cells | |
|---|---|---|
| | $EC_{50}$ (nM) | Emax |
| 38 | 10.7 | 102% |
| 39 | 9.5 | 99% |
| 40 | 31.9 | 103% |
| 41 | 45.0 | 106% |
| 42 | 250.8 | 104% |
| 43 | 190.3 | 104% |
| 44 | 82.0 | 101% |
| 45 | 125.6 | 98% |
| 46 | 26.7 | 82% |
| 47 | 116.9 | 94% |
| 48 | 19.5 | 91% |
| 49 | 22.2 | 95% |
| 50 | 4.42 | 90% |
| 51 | 18.6 | 98% |
| 52 | 9.15 | 94% |
| 53 | 76.2 | 75% |
| 54 | 22.0 | 96% |
| 55 | 4.9 | 88% |
| 56 | 12.3 | 95% |
| 57 | 24.4 | 91% |
| 58 | 41.0 | 93% |
| 59 | 29.8 | 86% |

The same experiment has been performed with peptides from the prior art (WO2015/157829) known under the names B7-33 C11.23S, AcB7-33 C11.23S and KKK(AcB7-29 C11.23S).

The following $EC_{50}$ results have been obtained for these three peptides.

TABLE 3

| Name | cAMP assay in OVCAR 5 cells | |
|---|---|---|
| | EC50 (nM) | Emax |
| B7-33 C11.23S | 1641 | 90% |
| AcB7-33 C11.23S | 929 | 70% |
| KKKK(AcB7-29 C11.23S) | 206 | 84% |

As demonstrated above, the peptides according to the invention possess very interesting RXFP1 agonist properties, and are very effective to activate RXFP1.

They are moreover all significantly and unexpectedly superior to the peptides from the prior art.

Example 4: Solubility Testing of Peptides of the Invention in Buffer

A. Method

Prior to the testing of solubility of a peptide batch, its purity (HPLC-UV) was determined.
Study Media:
Phosphate buffer 50 mM pH 6.5: 15.9 ml $Na_2HPO_4$ 0.1 M (Carlo Erba 480087)+34.1 ml $NaH_2PO_4$ 0.1 M (Carlo Erba 480141)+$H_2O$ MilliQ QSP 100 ml Phosphate buffer 50 mM pH 7.4: 40.5 ml $Na_2HPO_4$ 0.1 M (Carlo Erba 480087)+9.5 ml $NaH_2PO_4$ 0.1 M (Carlo Erba 480141)+$H_2O$ MilliQ QSP 100 ml Acetate Buffer 50 mM pH4.5: 0.75 g $C_2H_3O_2Na$, $3H_2O$ (Sigma S7545)+0.35 ml $CH_3CO_2H$ 100% solution dissolved in Millipore water, adjusted to pH with diluted (1:1) $CH_3CO_2H$ and diluted to 250 ml with Millipore water.

In a 4 ml Ependorph vial, an accurately weighed sample of compound was diluted in study media to obtain target concentration of 2, 6 or 10 mg/ml of pure compound. The sample vials were shacked (rock 'roll shaker) for ~19 h. 3004, Aliquots were filtered through a Millipore "Solvinert" plate (0.45 μm-PTFE hydrophilic). The solubility was then determined by comparison of a 0.2 pL-injection of the filtrate with the UV peak areas obtained with a stock solution of the peptide at a concentration of 1.2 mg/ml in DMSO (based on % purity), injecting various volumes ranging from 0.2-2 pL.

Analysis pH was measured with a micro electrode
HPLC Conditions:
Waters Acquity UPLC System with DAD detector
Column: Waters Peptide Column CSH C18 (130 Å; 1.7 μm; 50*2.1 mm)
Column temperature: 60° C.
Flow: 0.3 ml/min
Full loop (about 5 μL)—overfill factor 5
Weak et Strong wash: H2O/ACN (75/25; V/V); Seal wash: H2O/IsOH (95/5; V/V).
Mobile Phase:
Solvent A: 0.05% TFA in $H_2O$; Solvent B: 0.035% TFA in CH3CN
Gradient: from 0 to 12 min B=2% to 60%, from 12 to 14 min B=60% to 100%. Column washing 100% B 1 min, column equilibration 2% B 2.5 min.
UV detector: wavelength 220 nm.

B. Results

The solubility results obtained are represented in the following Table 4.

TABLE 4

| SEQ ID NO | Solubility Acetate buffer pH 4.5 | Solubility phosphate buffer pH 7.4 |
|---|---|---|
| 3 | ≥3.3 mg/ml* | ≥2.9 mg/ml* |
| 4 | ≥6.1 mg/ml** | ≥5.8 mg/ml** |
| 5 | =4.0 mg/ml** | =4.0 mg/ml** |
| 49 | ND | ≥2.5 mg/ml*** |
| 50 | ND | ≥2.3 mg/ml*** |
| 51 | ND | ≥2.4 mg/ml*** |
| 52 | ND | ≥2.3 mg/ml*** |
| 53 | ND | ≥2.1 mg/ml*** |
| 54 | ND | ≥2.4 mg/ml*** |
| 55 | ND | ≥2.5 mg/ml*** |
| 58 | ND | ≥2.0 mg/ml*** |
| 59 | ND | ≥2.4 mg/ml*** |

ND = Not determined;
*Target solubility: 3.0 mg/ml;
**Target solubility: 6.0 mg/ml;
***Target solubility 2.0 mg/ml The same experiment experiment has been performed with peptides from the prior art (WO2015/157829) known under the names B7-33 C11.23S, AcB7-33 C11.23S and KKK(AcB7-29 C11.23S).

The following solubility results have been obtained for these three peptides.

TABLE 5

| Name | Solubility Acetate buffer pH 4.5 | Solubility phosphate buffer pH 7.4 |
|---|---|---|
| B7-33 C11.23S | 1.9 mg/ml*** | 0.014 mg/ml*** |
| AcB7-33 C11.23S | 1.54 mg/ml*** | <0.001 mg/ml*** |
| KKKK(AcB7-29 C11.23S) | 2.3 mg/ml*** | 0.177 mg/ml*** |

***Target solubility 2.0 mg/ml

Example 5: Stability in Plasma

A. Method

Prior to the testing of stability in plasma of a peptide batch, its purity (HPLC-UV) was determined.
Study Media:
Rat and Human plasma: anti-coagulant sodium or lithium heparin.
Stock Solution:
100 μM solution of study compound in 50 mM Phosphate buffer pH 7.4.
950 μL plasma is pre-incubated for 5 min at 37° C. 50 μL of compound stock solution is added. Final compound concentration=5 μM. Vortex and transfer 1504, plasma into an Eppendorf for each time point. The time points 0-1 and −4 h are carried out in duplicate for each species.
After incubation extract 1504, plasma with 6004, Acetonitrile containing with 1% TFA. Vortex and centrifuge 10 min at 14600 rpm. Dry 2004, supernatant under $N_2$. Reconstitute sample in 200 μL of $H_2O/CH_3CN$ 98/2+0.1% FA+50 ng/ml Labetalol and analyze using the analytical system used in solubility and stability studies.
For determination of the amount of the remaining peptide, the peak areas of the target compound at t0 and each time point days were compared, resulting in "% remaining peptide", following the equation
% remaining peptide=[(peak area peptide time)×100]/ peak area peptide t0. The stability is expressed as "% remaining peptide".
Acceptance criteria The tests compounds were considered stable if precision was ~15% and the recovery was within 85-115% range.

B. Results

The Plasma stability results obtained are represented in the following Table 6.

TABLE 6

| | Human Plasma stability % remaining | | | Rat plasma stability % remaining | | |
|---|---|---|---|---|---|---|
| SEQ ID NO | T = 0 | 1 h | 4 h | T = 0 | 1 h | 4 h |
| 1 | 100 | 71 | 55 | 100 | 72 | 17 |
| 2 | 100 | 80 | 79 | 100 | 57 | 24 |
| 3 | 100 | 85 | 64 | 100 | 78 | 55 |
| 4 | 100 | 95 | 93 | 100 | 91 | 101 |
| 5 | 100 | 93 | 74 | 100 | 86 | 60 |

The same experiment has been performed with peptides from the prior art (WO2015/157829) known under the names B7-33 C11.23S, AcB7-33 C11.23S and KKK(AcB7-29 C11.23S).

The following plasma and blood stability results have been obtained for these three peptides.

TABLE 7

| Name | Human Plasma stability % remaining | | | Rat plasma stability % remaining | | |
|---|---|---|---|---|---|---|
| | T = 0 | 1 h | 4 h | T = 0 | 1 h | 4 h |
| B7-33 C11.23S | 100 | 18 | 3 | 100 | 15 | 2 |
| Ac B7-33 | 100 | 67 | 18 | 100 | 16 | 2 |
| KKKK(AcB7-29 C11.23S) | 100 | 41 | 31 | 100 | 23 | 14 |

```
                        Sequence listing

SEQ ID NO: 1
Ac-Leu-Glu-Gly-Arg-Glu-Lys-Val-Arg-Ala-Gln-Ile-Aib-Ile-Glu-Gly-Met-Ser-Lys-Trp-Ser-
Lys-Arg-Lys-Lys-NH2

SEQ ID NO: 2
Ac-Leu-Glu-Gly-Arg-Glu-Lys-Val-Arg-Ala-Gln-Ile-Aib-Aib-Glu-Gly-Met-Ser-Lys-Trp-Ser-
Lys-Arg-Lys-Lys-NH2

SEQ ID NO: 3
Ac-Leu-Glu-Gly-Arg-Glu-Lys-Val-Arg-Ala-Gln-Ile-Aib-Aib-Glu-Gly-Nle-Ser-Thr-Trp-Ser-
Aib-Arg-Lys-Lys-NH2

SEQ ID NO: 4
Ac-Leu-Glu-Gly-Arg-Glu-Lys-Val-Arg-Ala-Gln-Ile-Aib-Aib-Glu-Gly-Met-Ser-Thr-Trp-Ser-
Aib-Arg-Lys-Lys-NH2

SEQ ID NO: 5
Ac-Leu-Glu-Gly-Arg-Glu-Lys-Val-Arg-Ala-K(Ac)-Ile-Aib-Aib-Glu-Gly-Nle-Ser-Thr-Trp-
Ser-Aib-Arg-Lys-K(Ac)-NH2

SEQ ID NO: 6
H-Leu-Glu-Gly-Arg-Glu-Lys-Val-Arg-Ala-Gln-Ile-Aib-Ile-Glu-Gly-Met-Ser-Lys-Trp-Ser-
Lys-Arg-Lys-Lys-NH2

SEQ ID NO: 7
Ac-Leu-Glu-Gly-Arg-Glu-Lys-Val-Arg-Aib-Gln-Ile-Aib-Ile-Glu-Gly-Met-Ser-Lys-Trp-Ser-
Lys-Arg-Lys-Lys-NH2

SEQ ID NO: 8
Ac-Leu-Glu-Gly-Arg-Glu-Lys-Val-Arg-Ala-Gln-Ile-Aib-Ile-Glu-Gly-Nle-Ser-Lys-Trp-Ser-
Lys-Arg-Lys-Lys-NH2

SEQ ID NO: 9
Ac-Leu-Glu-Gly-Arg-Glu-Lys-Val-Arg-Ala-Gln-Ile-Aib-Ile-Glu-Gly-Met-Ser-Lys-(1-Nal)-
Ser-Lys-Arg-Lys-Lys-NH2

SEQ ID NO: 10
Ac-Leu-Glu-Gly-Arg-Glu-Lys-Val-Arg-Ala-Gln-Ile-Aib-Aib-Glu-Gly-Met-Ser-Thr-Trp-Ser-
Lys-Arg-Lys-Lys-NH2

SEQ ID NO: 11
Ac-Aib-Glu-Gly-Arg-Glu-Lys-Val-Arg-Ala-Gln-Ile-Aib-Aib-Glu-Gly-Met-Ser-Lys-Trp-Ser-
Lys-Arg-Lys-Lys-NH2

SEQ ID NO: 12
H-Aib-Glu-Gly-Arg-Glu-Lys-Val-Arg-Ala-Gln-Ile-Aib-Aib-Glu-Gly-Met-Ser-Lys-Trp-Ser-
Lys-Arg-Lys-Lys-NH2

SEQ ID NO: 13
Ac-Leu-Glu-Gly-Arg-Glu-Lys-Val-Arg-Ala-Gln-Ile-Aib-Aib-Glu-Gly-Nle-Ser-Thr-Trp-Ser-
Lys-Arg-Lys-Lys-NH2

SEQ ID NO: 14
Ac-Leu-Glu-Gly-Arg-Glu-Lys-Val-Arg-Ala-Gln-Ile-Aib-Aib-Glu-Gly-Nle-Ser-Lys-(1-Nal)-
Ser-Lys-Arg-Lys-Lys-NH2

SEQ ID NO: 15
Ac-Leu-Glu-Gly-Arg-Glu-Lys-Val-Arg-Ala-Gln-Ile-Aib-Aib-Glu-Gly-Nle-Ser-Thr-(1-Nal)-
Ser-Lys-Arg-Lys-Lys-NH2

SEQ ID NO: 16
Ac-Leu-Glu-Gly-Arg-Glu-Lys-Val-Arg-Ala-Ala-Ile-Aib-Aib-Glu-Gly-Met-Ser-Thr-Trp-Ser-
Lys-Arg-Lys-Lys-NH2
```

Sequence listing

SEQ ID NO: 17
Ac-Leu-Glu-Gly-Arg-Glu-Lys-Val-Arg-Ala-Ala-Ile-Aib-Aib-Glu-Gly-Nle-Ser-Thr-Trp-Ser-
Aib-Arg-Lys-Lys-NH$_2$

SEQ ID NO: 18
Ac-Leu-Glu-Gly-Arg-Glu-Lys-Val-Arg-Ala-Ala0-Ile-Aib-Aib-Glu-Gly-Met-Ser-Lys-Trp-Ser-
Aib-Arg-Lys-NH$_2$

SEQ ID NO: 19
Ac-Leu-Glu-Gly-Arg-Glu-Lys-Val-Arg-Ala-Aib-Ile-Aib-Aib-Glu-Gly-Nle-Ser-Thr-Trp-Ser-
Lys-Arg-Lys-Lys-NH$_2$

SEQ ID NO: 20
Ac-Leu-Glu-Gly-Arg-Glu-Lys-Val-Arg-Ala-Aib-Ile-Aib-Aib-Glu-Gly-Nle-Ser-Thr-Trp-Ser-
Mly-Arg-Lys-Lys-NH$_2$

SEQ ID NO: 21
Ac-Leu-Glu-Gly-Arg-Glu-Lys-Val-Arg-Ala-Gln-Ile-Aib-Aib-Glu-Gly-Nle-Ser-Thr-Trp-Ser-
Aib-Arg-Lys-K(Ac)-NH$_2$

SEQ ID NO: 22
Ac-Leu-Glu-Gly-Arg-Glu-Lys-Val-Arg-Ala-Gln-Ile-Aib-Aib-Glu-Gly-Nle-Ser-Thr-Trp-Ala-
Aib-Arg-Lys-Lys-NH$_2$

SEQ ID NO: 23
Ac-Leu-Glu-Gly-Arg-Glu-Lys-Val-Arg-Ala-Gln-Ile-Aib-Aib-Glu-Gly-Nle-Ser-Thr-Trp-Thr-
Aib-Arg-Lys-Lys-NH$_2$

SEQ ID NO: 24
Ac-Leu-Glu-Gly-Arg-Glu-Lys-Val-Arg-Ala-K(Ac)-Ile-Aib-Aib-Glu-Gly-Nle-Ser-Thr-Trp-Ser-
Aib-Arg-Lys-Lys-NH$_2$

SEQ ID NO: 25
Ac-Leu-Glu-Gly-Arg-Glu-Lys-Val-Arg-Ala-K(Ac)-Ile-Aib-Aib-Glu-Gly-Nle-Ser-Thr-Trp-Ser-
K(Ac)-Arg-Lys-Lys-Lys-NH$_2$

SEQ ID NO: 26
Ac-Leu-Glu-Gly-Arg-Glu-Lys-Val-Arg-Ala-K(Ac)-Ile-Aib-Aib-Glu-Gly-Nle-Ser-Thr-Trp-Ser-
K(Ac)-Arg-Lys-Lys-K(Ac)-NH$_2$

SEQ ID NO: 27
Ac-Leu-Glu-Gly-Arg-Glu-Lys-Val-Arg-Ala-K(Ac)-Ile-Aib-Aib-Glu-Gly-Nle-Ser-Thr-Trp-Ser-
Aib-Arg-Lys-K(Ac)-Lys-NH$_2$

SEQ ID NO: 28
Ac-Leu-Glu-Gly-Arg-Glu-Lys-Val-Arg-Ala-K(Ac)-Ile-Aib-Aib-Glu-Gly-Nle-Ser-Thr-Trp-Ser-
Aib-Arg-Lys-K(Ac)-K(Ac)-NH$_2$

SEQ ID NO: 29
Ac-Leu-Glu-Gly-Arg-Glu-Lys-Val-Arg-Ala-K(Ac)-Ile-Aib-Aib-Glu-Gly-Nle-Ser-Thr-(1-Nal)-
Ser-Aib-Arg-Lys-K(Ac)-NH$_2$

SEQ ID NO: 30
Ac-Leu-Glu-Gly-Arg-Glu-Lys-Val-Arg-Ala-K(Ac)-Ile-Aib-Aib-Glu-Gly-Nle-Ser-Thr-Trp-Mse-
Aib-Arg-Lys-K(Ac)-NH$_2$

SEQ ID NO: 31
Ac-Leu-Glu-Gly-Arg-Glu-Lys-Val-Arg-Ala-K(Ac)-Ile-Aib-Aib-Glu-Gly-Nle-Ser-Thr-Trp-Ser-
Aib-Arg-Lys-Gln-NH$_2$

SEQ ID NO: 32
Ac-Leu-Glu-Gly-Arg-Glu-Lys-Val-Arg-Ala-K(Ac)-Ile-Aib-Aib-Glu-Gly-Nle-Ser-Thr-Trp-Ser-
Aib-Arg-Lys-Leu-NH$_2$

SEQ ID NO: 33
Ac-Leu-Glu-Gly-Arg-Glu-Lys-Val-Arg-K(Ac)-Gln-Ile-Aib-Aib-Glu-Gly-Nle-Ser-Thr-Trp-Ser-
Aib-Arg-Lys-Lys-NH$_2$

SEQ ID NO: 34
Ac-Leu-Glu-Gly-Arg-Glu-Lys-Val-Arg-K(Ac)-Aib-Ile-Aib-Aib-Glu-Gly-Nle-Ser-Thr-Trp-Ser-
Aib-Arg-Lys-Lys-NH$_2$

SEQ ID NO: 35
Ac-Leu-Glu-Gly-Arg-Glu-Lys-Val-Arg-Ala-Gln-Ile-Aib-Aib-Glu-Gly-Gln-Ser-Thr-Trp-Ser-
Aib-Arg-Lys-Lys-NH$_2$

Sequence listing

SEQ ID NO: 36
Ac-Leu-Glu-Gly-Arg-Glu-Lys-Val-Arg-Ala-Gln-Ile-Aib-Aib-Glu-Gly-Nle-Ser-Lys-(1-Nal)-Ser-Lys-Arg-NH$_2$

SEQ ID NO: 37
Ac-Leu-Glu-Gly-Arg-Glu-Lys-Val-Arg-Ala-Gln-Ile-Aib-Aib-Glu-Gly-Nle-Ser-Thr-(1-Nal)-Ser-Lys-Arg-NH$_2$

SEQ ID NO: 38
Ac-Leu-Glu-Gly-Arg-Glu-Lys-Val-Arg-Ala-Gln-Ile-Aib-Aib-Glu-Gly-Met-Ser-Lys-Trp-Ser-Lys-Arg-NH$_2$

SEQ ID NO: 39
Ac-Leu-Glu-Gly-Arg-Glu-Lys-Val-Arg-Ala-Gln-Ile-Aib-Aib-Glu-Gly-Met-Ser-Mse-Trp-Ser-Lys-Arg-NH$_2$

SEQ ID NO: 40
Ac-Leu-Glu-Gly-Arg-Glu-Lys-Val-Arg-Ala-Gln-Ile-Aib-Aib-Glu-Gly-Met-Ser-Thr-Trp-Ser-Lys-Arg-NH$_2$

SEQ ID NO: 41
Ac-Leu-Glu-Gly-Arg-Glu-Lys-Val-Arg-Ala-Gln-Ile-Aib-Aib-Glu-Gly-Met-Ser-Thr-Trp-Ser-Aib-Arg-NH$_2$

SEQ ID NO: 42
Ac-Leu-Glu-Gly-Arg-Glu-Lys-Val-Arg-Aib-Gln-Ile-Aib-Aib-Glu-Gly-Met-Ser-Thr-Trp-Ser-Aib-Arg-NH$_2$

SEQ ID NO: 43
Ac-Leu-Glu-Gly-Arg-Glu-Lys-Val-Arg-Ala-Aib-Ile-Aib-Aib-Glu-Gly-Met-Ser-Thr-Trp-Ser-Aib-Arg-NH$_2$

SEQ ID NO: 44
Ac-Leu-Glu-Gly-Arg-Glu-Lys-Val-Arg-Ala-Gln-Ile-Aib-Aib-Glu-Gly-Nle-Ser-Thr-Trp-Ser-Aib-Arg-Lys-NH$_2$

SEQ ID NO: 45
Ac-Leu-Glu-Gly-Arg-Glu-Lys-Val-Arg-Ala-Gln-Ile-Aib-Aib-Glu-Gly-Met-Ser-Thr-Trp-Ser-Aib-Arg-Lys-NH$_2$

SEQ ID NO: 46
Ac-Leu-Glu-Gly-Arg-Glu-Lys-Val-Arg-Ala-Gln-Ile-Aib-Aib-Glu-Gly-Met-Ser-Lys-Trp-Ser-Aib-Arg-NH$_2$

SEQ ID NO: 47
Ac-Leu-Glu-Gly-Arg-Glu-Lys-Val-Arg-Ala-K(Ac)-Ile-Aib-Aib-Glu-Gly-Nle-Ser-Thr-Trp-Ser-Aib-Arg-Lys-NH$_2$

SEQ ID NO: 48
Ac-Glu-Leu-Glu-Gly-Arg-Glu-Lys-Val-Arg-Ala-Ala-Ile-Aib-Aib-Glu-Gly-Nle-Ser-Thr-Trp-Ser-Aib-Arg-Lys-Lys-NH$_2$

SEQ ID NO: 49
Ac-Leu-Glu-Gly-Arg-Glu-Lys-Val-Arg-Arg-Gln-Ile-Aib-Aib-Glu-Gly-Nle-Ser-Thr-Trp-Ser-Aib-Arg-Lys-Lys-NH$_2$

SEQ ID NO: 50
Ac-Leu-Glu-Gly-Arg-Glu-Lys-Val-Arg-Ala-Gln-Ile-Aib-Aib-Glu-Gly-Nle-Ser-Thr-Trp-Ser-Aib-Arg-Arg-Arg-NH$_2$

SEQ ID NO: 51
Ac-Leu-Glu-Gly-Arg-Glu-Lys-Val-Arg-Ala-Gln-Ile-Aib-Aib-Glu-Gly-Nle-Ser-Thr-Phe-Ser-Aib-Arg-Lys-Lys-NH$_2$

SEQ ID NO: 52
Ac-Leu-Glu-Gly-Arg-Glu-Lys-Val-Arg-Ala-Gln-Ile-Aib-Aib-Glu-Gly-Nle-Ser-Gln-Trp-Ser-Aib-Arg-Arg-Arg-NH$_2$

SEQ ID NO: 53
Ac-Leu-Glu-Gly-Arg-Glu-Lys-Val-Arg-Ala-Gln-Ile-Aib-Aib-Glu-Gly-Nle-Ser-Thr-Tyr-Ser-Aib-Arg-Lys-Lys-NH$_2$

SEQ ID NO: 54
Ac-Leu-Glu-Gly-Arg-Glu-Lys-Val-Arg-Ala-Gln-Ile-Aib-Aib-Glu-Gly-Gln-Ser-Thr-Trp-Ser-Aib-Arg-Lys-Lys-NH$_2$

Sequence listing

SEQ ID NO: 55
Ac-Leu-Glu-Gly-Arg-Glu-Lys-Val-Arg-Ala-Gln-Ile-Aib-Aib-Glu-Gly-Nle-Ser-Arg-Trp-Ser-Aib-Arg-Arg-Arg-NH$_2$

SEQ ID NO: 56
Ac-Mel-Glu-Gly-Arg-Glu-Lys-Val-Arg-Ala-K(Ac)-Ile-Aib-Aib-Glu-Gly-Nle-Ser-Thr-Trp-Ser-Aib-Arg-Lys-K(Ac)-NH$_2$

SEQ ID NO: 57
Ac-Leu-Glu-Gly-Arg-Glu-Lys-Val-Arg-Ala-Gln-Ile-Aib-Aib-Glu-Gly-Gln-Ser-Thr-Phe-Ser-Aib-Arg-Lys-Lys-NH$_2$

SEQ ID NO: 58
Ac-Leu-Glu-Gly-Arg-Glu-Lys-Val-Arg-Ala-Gln-Ile-Aib-Aib-Glu-Gly-Gln-Ser-Thr-Tyr-Ser-Aib-Arg-Lys-Lys-NH$_2$

SEQ ID NO: 59
Ac-Leu-Glu-Gly-Arg-Glu-Lys-Val-Arg-Ala-Gln-Ile-Aib-Aib-Glu-Gly-Gln-Ser-Thr-Pfp-Ser-Aib-Arg-Lys-Lys-NH$_2$

SEQ ID NO: 60: H2-relaxin A chain
H-Gln-Leu-Tyr-Ser-Ala-Leu-Ala-Asn-Lys-Cys-Cys-His-Val-Gly-Cys-Thr-Lys-Arg-Ser-Leu-Ala-Arg-Phe-Cys-OH SEQ ID NO: 61: H2-relaxin B chain
H-Asp-Ser-Trp-Met-Glu-Glu-Val-Ile-Lys-Leu-Cys-Gly-Arg-Glu-Leu-Val-Arg-Ala-Gln-Ile-Ala-Ile-Cys-Gly-Met-Ser-Thr-Trp-Ser-OH SEQ ID NO: 62: SEQ ID B7-33 C11.23S*
H-Val-Ile-Lys-Leu-Ser-Gly-Arg-Glu-Leu-Val-Arg-Ala-Gln-Ile-Ala-Ile-Ser-Gly-Met-Ser-Thr-Trp-Ser-Lys-Arg-Ser-Leu-NH$_2$ SEQ ID NO: 63: SEQ ID AcB7-33 C11.23S*
Ac-Val-Ile-Lys-Leu-Ser-Gly-Arg-Glu-Leu-Val-Arg-Ala-Gln-Ile-Ala-Ile-Ser-Gly-Met-Ser-Thr-Trp-Ser-Lys-Arg-Ser-Leu-NH$_2$ SEQ ID NO: 64: SEQ ID KKKK (AcB7-29 C11.23S)*
Ac-Val-Ile-Lys-Leu-Ser-Gly-Arg-Glu-Leu-Val-Arg-Ala-Gln-Ile-Ala-Ile-Ser-Gly-Met-Ser-Thr-Trp-Ser-Lys-Lys-Lys-Lys-NH$_2$

*comparison examples

---

The invention claimed is:

1. The peptide having the following formula (I)

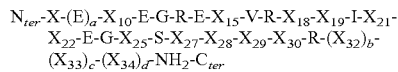

$N_{ter}$-X-(E)$_a$-X$_{10}$-E-G-R-E-X$_{15}$-V-R-X$_{18}$-X$_{19}$-I-X$_{21}$-X$_{22}$-E-G-X$_{25}$-S-X$_{27}$-X$_{28}$-X$_{29}$-X$_{30}$-R-(X$_{32}$)$_b$-(X$_{33}$)$_c$-(X$_{34}$)$_d$-NH$_2$-C$_{ter}$ wherein:
$N_{ter}$ represents the N-terminal end of the peptide;
$C_{ter}$ represents the C-terminal end of the peptide;
a, b, c and d independently represent 0 or 1;
X represents hydrogen atom or acetyl group;
E represents glutamic acid;
$X_{10}$ represents an amino acid selected from the group consisting of leucine, 2-amino-isobutyric acid, α-methyl-leucine and Nε-acetyl-lysine;
G represents glycine;
R represents arginine;
$X_{15}$ represents an amino acid selected from the group consisting of lysine, homolysine, arginine, homoarginine and ornithine;
V represents valine;
$X_{18}$ represents an amino acid selected from the group consisting of alanine, 2-amino-isobutyric acid, Nε-acetyl-lysine, arginine, leucine and glutamine;
$X_{19}$ represents an amino acid selected from the group consisting of glutamine, Nε-acetyl-lysine, alanine and 2-amino-isobutyric acid;
I represents isoleucine;
$X_{21}$ represents an amino acid selected from the group consisting of alanine and 2-amino-isobutyric acid;
$X_{22}$ represents an amino acid selected from the group consisting of isoleucine and 2-amino-isobutyric acid;
$X_{25}$ represents an amino acid selected from the group consisting of methionine, norleucine, glutamine, glutamic acid and Nε-acetyl-lysine;
S represents serine;
$X_{27}$ represents an amino acid selected from the group consisting of threonine, lysine, α-methyl-serine, glutamine and arginine;
$X_{28}$ represents an amino acid selected from the group consisting of tryptophan, 5-chlorotryptophan, 5-Fluorotryptophan, 5-MethoxyTryptophan, phenylalanine, homophenylalanine, tyrosine, 4-fluoro-phenylalanine, 1-naphtylalanine and 2-naphtylalanine;
$X_{29}$ represents an amino acid selected from the group consisting of serine, alanine, threonine, α-methyl-serine, Nε-acetyl-lysine and valine;
$X_{30}$ represents an amino acid selected from the group consisting of lysine, 2-amino-isobutyric acid, α-methyl-lysine, Nε-acetyl-lysine and arginine;
$X_{32}$ represents an amino acid selected from the group consisting of lysine, arginine and Nε-acetyl-lysine;
$X_{33}$ represents an amino acid selected from the group consisting of leucine, lysine, Nε-acetyl-lysine, glutamine, arginine and alanine; and
$X_{34}$ represents an amino acid selected from the group consisting of lysine and Nε-acetyl-lysine;
or a salt or a solvate thereof.

2. The peptide according to claim 1, wherein $X_{21}$ represents 2-amino-isobutyric acid or a salt or a solvate thereof.

3. The peptide according to claim 1, wherein $X_{25}$ represents an amino acid selected from the group consisting of methionine, norleucine and glutamine or a salt or a solvate thereof.

4. The peptide according to claim 1 having the following formula (Ia) (SEQ ID NO:66):

$N_{ter}$-X-(E)$_a$-X$_{10}$-E-G-R-E-X$_{15}$-V-R-X$_{18}$-X$_{19}$-I-X$_{21}$-X$_{22}$-E-G-X$_{25}$-S-X$_{27}$-X$_{28}$-X$_{29}$-X$_{30}$-R-(X$_{32}$)$_b$-(X$_{33}$)$_c$-(X$_{34}$)$_d$-NH$_2$-C$_{ter}$ wherein:
$N_{ter}$ represents the N-terminal end of the peptide;
$C_{ter}$ represents the C-terminal end of the peptide;
a, b, c and d independently represent 0 or 1;
X represents hydrogen atom or acetyl group;
E represents glutamic acid;
$X_{10}$ represents an amino acid selected from the group consisting of leucine, 2-amino-isobutyric acid and α-methyl-leucine;
G represents glycine;
R represents arginine;
K represents lysine;
V represents valine;
$X_{18}$ represents an amino acid selected from the group consisting of alanine, 2-amino-isobutyric acid, Nε-acetyl-lysine and arginine;
$X_{19}$ represents an amino acid selected from the group consisting of glutamine, Nε-acetyl-lysine, alanine and 2-amino-isobutyric acid;
I represents isoleucine;
Aib represents 2-amino-isobutyric acid;
$X_{22}$ represents an amino acid selected from the group consisting of isoleucine and 2-amino-isobutyric acid;
$X_{25}$ represents an amino acid selected from the group consisting of methionine, norleucine and glutamine;
S represents serine;
$X_{27}$ represents an amino acid selected from the group consisting of threonine, lysine, α-methyl-serine, glutamine and arginine;
$X_{28}$ represents an amino acid selected from the group consisting of tryptophan, 1-naphtylalanine, phenylalanine, tyrosine and 4-fluoro-phenylalanine;
$X_{29}$ represents an amino acid selected from the group consisting of serine, alanine, threonine and α-methyl-serine;
$X_{30}$ represents an amino acid selected from the group consisting of lysine, 2-amino-isobutyric acid, α-methyl-lysine and Nε-acetyl-lysine;
$X_{32}$ represents an amino acid selected from the group consisting of lysine and arginine;
$X_{33}$ represents an amino acid selected from the group consisting of leucine, lysine, Nε-acetyl-lysine, glutamine and arginine; and
$X_{34}$ represents an amino acid selected from the group consisting of lysine and Nε-acetyl-lysine;
or a salt or a solvate thereof.

5. The peptide according to claim 1, wherein it has an amino acid sequence selected from the group consisting of the amino acid sequences of reference SEQ ID NO: 1 to 59.

6. The peptide according to claim 1, wherein $X_{18}$ represents an amino acid selected from the group consisting of alanine and arginine or a salt or a solvate thereof.

7. The peptide according to claim 1, wherein $X_{29}$ represents an amino acid selected from the group consisting of serine and α-methyl-serine or a salt or a solvate thereof.

8. The peptide according to claim 4, wherein said peptide has formula (Ia) wherein:

$N_{ter}$ represents the N-terminal end of the peptide;
$C_{ter}$ represents the C-terminal end of the peptide;
X represents hydrogen atom or acetyl group;
a represents 0 or 1;
E represents glutamic acid;
$X_{10}$ represents an amino acid selected from the group consisting of leucine, 2-amino-isobutyric acid and α-methyl-leucine;
G represents glycine;
R represents arginine;
K represents lysine;
V represents valine;
$X_{18}$ represents an amino acid selected from the group consisting of alanine and arginine;
$X_{19}$ represents an amino acid selected from the group consisting of glutamine, Nε-acetyl-lysine, alanine and 2-amino-isobutyric acid;
I represents isoleucine;
Aib represents 2-amino-isobutyric acid;
$X_{22}$ represents an amino acid selected from the group consisting of isoleucine and 2-amino-isobutyric acid;
$X_{25}$ represents an amino acid selected from the group consisting of methionine, norleucine and glutamine;
S represents serine;
$X_{27}$ represents an amino acid selected from the group consisting of threonine, lysine, α-methyl-serine, glutamine and arginine;
$X_{28}$ represents an amino acid selected from the group consisting of tryptophan, 1-naphtylalanine, phenylalanine, tyrosine and 4-fluoro-phenylalanine;
$X_{29}$ represents an amino acid selected from the group consisting of serine and α-methyl-serine;
$X_{30}$ represents an amino acid selected from the group consisting of lysine, 2-amino-isobutyric acid, α-methyl-lysine and Nε-acetyl-lysine;
(i) b represents 0; or (ii) b represents 1 and $X_{32}$ represents an amino acid selected from the group consisting of lysine and arginine;
(i) c represents 0 or (ii) c represents 1 and $X_{33}$ represents an amino acid selected from the group consisting of leucine, lysine, Nε-acetyl-lysine and arginine; and
(i) d represents 0 or (ii) d represents 1 and $X_{34}$ represents an amino acid selected from the group consisting of lysine and Nε-acetyl-lysine;

or a salt or a solvate thereof.

9. The peptide according to claim 1, having an amino acid sequence selected from the group consisting of SEQ ID NO: 1-6, 9-17, 19-21, 24-30, 32, 35, 38-41, 46, 48-52 and 54-59.

10. The peptide according to claim 1, having an amino acid sequence selected from the group consisting of SEQ ID NO: 2-5, 13, 16, 17, 19, 20, 25-27, 29, 35, 38, 39, 48, 50-52, 55 and 56.

11. The peptide according to claim 1, having an amino acid sequence selected from the group consisting of SEQ ID NO: 5, 16, 20, 25, 27, 39, 50, 52 and 55.

12. The peptide according to claim 1, having an amino acid sequence selected from the group consisting of SEQ ID NO: 16, 20, 25, 50 and 55.

13. A pharmaceutical composition comprising at least one peptide according to claim 1, or a pharmaceutically acceptable salt or solvate thereof, and at least one pharmaceutically acceptable carrier.

14. A method for treating a disease or condition implicating the Relaxin family peptide receptor 1 (RXFP1) comprising administering to an individual in need of said treatment a peptide according to claim 1, or a pharmaceutically acceptable salt or solvate thereof.

15. The method according to claim 14, wherein the disease or condition is selected from the group consisting of fibrosis, fibrotic diseases, idiopathic pulmonary fibrosis, kidney diseases involving fibrosis, pulmonary hypertension, and preeclampsia.

16. The method according to claim 14, wherein the disease or condition is selected from the group consisting of heart disease and vascular disease.

17. The method according to claim 16, wherein the disease or condition is selected from the group consisting of acute or chronic heart failure, systolic or diastolic heart failure, coronary artery disease, atherosclerosis, microvascular angina, and cardiovascular complication of diabetes.

18. The method according to claim 14, wherein the diseases or conditions is a renal failure.

19. The method according to claim 18, wherein the disease or condition is selected from renal dysfunction in cirrhosis, chronic kidney disease, and acute kidney injury.

20. The method according to claim 14, wherein the disease or condition is fibrotic disease selected from the group consisting of systemic sclerosis, scleroderma, and fibromyalgia.

* * * * *

SEQUENCE LISTING

<160> NUMBER OF SEQ ID NOS: 67

<210> SEQ ID NO 1
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 1

Leu Glu Gly Arg Glu Lys Val Arg Ala Gln Ile Xaa Ile Glu Gly Met
1               5                   10                  15

Ser Lys Trp Ser Lys Arg Lys Lys
            20

<210> SEQ ID NO 2
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 2

Leu Glu Gly Arg Glu Lys Val Arg Ala Gln Ile Xaa Xaa Glu Gly Met
1               5                   10                  15

Ser Lys Trp Ser Lys Arg Lys Lys
            20

<210> SEQ ID NO 3
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine or Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 3

Leu Glu Gly Arg Glu Lys Val Arg Ala Gln Ile Xaa Xaa Glu Gly Xaa
1               5                   10                  15

Ser Thr Trp Ser Xaa Arg Lys Lys
                20

<210> SEQ ID NO 4
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 4

Leu Glu Gly Arg Glu Lys Val Arg Ala Gln Ile Xaa Xaa Glu Gly Met
1               5                   10                  15

Ser Thr Trp Ser Xaa Arg Lys Lys
                20

<210> SEQ ID NO 5
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine,

```
            Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: Amino acid at position 24 is
      N-epsilon-Acetyl-lysine, 2-amino-4-acetamido-hexanoic acid (K(Ac))
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 5

Leu Glu Gly Arg Glu Lys Val Arg Ala Xaa Ile Xaa Xaa Glu Gly Xaa
1               5                   10                  15

Ser Thr Trp Ser Xaa Arg Lys Xaa
            20

<210> SEQ ID NO 6
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with a hydrogen atom
      (H) on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 6

Leu Glu Gly Arg Glu Lys Val Arg Ala Gln Ile Xaa Ile Glu Gly Met
1               5                   10                  15

Ser Lys Trp Ser Lys Arg Lys Lys
            20

<210> SEQ ID NO 7
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Amino acid at position 9 is 2-amino-isobutyric
      acid (Aib)
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
```

```
<221> NAME/KEY: VARIANT
<222> LOCATION: 24
<223> OTHER INFORMATION: The peptide is substituted with an -NH2 group
      on its C-terminal extremity

<400> SEQUENCE: 7

Leu Glu Gly Arg Glu Lys Val Arg Xaa Gln Ile Xaa Ile Glu Gly Met
1               5                  10                  15

Ser Lys Trp Ser Lys Arg Lys Lys
            20

<210> SEQ ID NO 8
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 8

Leu Glu Gly Arg Glu Lys Val Arg Ala Gln Ile Xaa Ile Glu Gly Xaa
1               5                  10                  15

Ser Lys Trp Ser Lys Arg Lys Lys
            20

<210> SEQ ID NO 9
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 19
<223> OTHER INFORMATION: Amino acid at position 19 is 1-Naphtylalanine
      (1-Nal)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 9
```

```
Leu Glu Gly Arg Glu Lys Val Arg Ala Gln Ile Xaa Ile Glu Gly Met
1               5                   10                  15

Ser Lys Xaa Ser Lys Arg Lys Lys
            20
```

<210> SEQ ID NO 10
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac) group on its N-terminal extremity
<220> FEATURE:
<221> NAME/KEY: VARIANT
<222> LOCATION: 12
<223> OTHER INFORMATION: Amino acid at position 12 is 2-amino-isobutyric acid (Aib)
<220> FEATURE:
<221> NAME/KEY: VARIANT
<222> LOCATION: 13
<223> OTHER INFORMATION: Amino acid at position 13 is 2-amino-isobutyric acid (Aib)
<220> FEATURE:
<221> NAME/KEY: VARIANT
<222> LOCATION: 24
<223> OTHER INFORMATION: The peptide is substituted with an -NH2 group on its C-terminal extremity

<400> SEQUENCE: 10

```
Leu Glu Gly Arg Glu Lys Val Arg Ala Gln Ile Xaa Xaa Glu Gly Met
1               5                   10                  15

Ser Thr Trp Ser Lys Arg Lys Lys
            20
```

<210> SEQ ID NO 11
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac) group on its N-terminal extremity
<220> FEATURE:
<221> NAME/KEY: VARIANT
<222> LOCATION: 1
<223> OTHER INFORMATION: Amino acid at position 1 is 2-amino-isobutyric acid (Aib)
<220> FEATURE:
<221> NAME/KEY: VARIANT
<222> LOCATION: 12
<223> OTHER INFORMATION: Amino acid at position 12 is 2-amino-isobutyric acid (Aib)
<220> FEATURE:
<221> NAME/KEY: VARIANT
<222> LOCATION: 13
<223> OTHER INFORMATION: Amino acid at position 13 is 2-amino-isobutyric acid (Aib)
<220> FEATURE:
<221> NAME/KEY: VARIANT
<222> LOCATION: 24
<223> OTHER INFORMATION: The peptide is substituted with an -NH2 group on its C-terminal extremity

<400> SEQUENCE: 11

```
Xaa Glu Gly Arg Glu Lys Val Arg Ala Gln Ile Xaa Xaa Glu Gly Met
1               5                   10                  15
```

```
Ser Lys Trp Ser Lys Arg Lys Lys
            20

<210> SEQ ID NO 12
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with a hydrogen atom
      (H) on its N-terminal extremity
<220> FEATURE:
<221> NAME/KEY: VARIANT
<222> LOCATION: 1
<223> OTHER INFORMATION: Amino acid at position 1 is 2-amino-isobutyric
      acid (Aib)
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 12

Xaa Glu Gly Arg Glu Lys Val Arg Ala Gln Ile Xaa Xaa Glu Gly Met
1               5                   10                  15

Ser Lys Trp Ser Lys Arg Lys Lys
            20

<210> SEQ ID NO 13
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 13
```

```
Leu Glu Gly Arg Glu Lys Val Arg Ala Gln Ile Xaa Xaa Glu Gly Xaa
1               5                   10                  15

Ser Thr Trp Ser Lys Arg Lys Lys
            20
```

<210> SEQ ID NO 14
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac) group on its N-terminal extremity
<220> FEATURE:
<221> NAME/KEY: VARIANT
<222> LOCATION: 12
<223> OTHER INFORMATION: Amino acid at position 12 is 2-amino-isobutyric acid (Aib)
<220> FEATURE:
<221> NAME/KEY: VARIANT
<222> LOCATION: 13
<223> OTHER INFORMATION: Amino acid at position 13 is 2-amino-isobutyric acid (Aib)
<220> FEATURE:
<221> NAME/KEY: VARIANT
<222> LOCATION: 16
<223> OTHER INFORMATION: Amino acid at position 16 is 2-amino hexanoic acid (Norleucine, Nle)
<220> FEATURE:
<221> NAME/KEY: VARIANT
<222> LOCATION: 19
<223> OTHER INFORMATION: Amino acid at position 19 is 1-Naphtylalanine (1-Nal)
<220> FEATURE:
<221> NAME/KEY: VARIANT
<222> LOCATION: 24
<223> OTHER INFORMATION: The peptide is substituted with an -NH2 group on its C-terminal extremity

<400> SEQUENCE: 14

```
Leu Glu Gly Arg Glu Lys Val Arg Ala Gln Ile Xaa Xaa Glu Gly Xaa
1               5                   10                  15

Ser Lys Xaa Ser Lys Arg Lys Lys
            20
```

<210> SEQ ID NO 15
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac) group on its N-terminal extremity
<220> FEATURE:
<221> NAME/KEY: VARIANT
<222> LOCATION: 12
<223> OTHER INFORMATION: Amino acid at position 12 is 2-amino-isobutyric acid (Aib)
<220> FEATURE:
<221> NAME/KEY: VARIANT
<222> LOCATION: 13
<223> OTHER INFORMATION: Amino acid at position 13 is 2-amino-isobutyric acid (Aib)
<220> FEATURE:
<221> NAME/KEY: VARIANT
<222> LOCATION: 16
<223> OTHER INFORMATION: Amino acid at position 16 is 2-amino hexanoic -continued

```
      acid (Norleucine, Nle)
<220> FEATURE:
<221> NAME/KEY: VARIANT
<222> LOCATION: 19
<223> OTHER INFORMATION: Amino acid at position 19 is 1-Naphtylalanine
      (1-Nal)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 15

Leu Glu Gly Arg Glu Lys Val Arg Ala Gln Ile Xaa Xaa Glu Gly Xaa
1               5                   10                  15

Ser Thr Xaa Ser Lys Arg Lys Lys
            20

<210> SEQ ID NO 16
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 16

Leu Glu Gly Arg Glu Lys Val Arg Ala Ala Ile Xaa Xaa Glu Gly Met
1               5                   10                  15

Ser Thr Trp Ser Lys Arg Lys Lys
            20

<210> SEQ ID NO 17
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
```

```
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 17

Leu Glu Gly Arg Glu Lys Val Arg Ala Ala Ile Xaa Xaa Glu Gly Xaa
1               5                   10                  15

Ser Thr Trp Ser Xaa Arg Lys Lys
            20

<210> SEQ ID NO 18
<211> LENGTH: 23
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 23
<223> OTHER INFORMATION: The peptide is substituted with an -NH2 group
      on its C-terminal extremity

<400> SEQUENCE: 18

Leu Glu Gly Arg Glu Lys Val Arg Ala Ala Ile Xaa Xaa Glu Gly Met
1               5                   10                  15

Ser Lys Trp Ser Xaa Arg Lys
            20

<210> SEQ ID NO 19
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
```

```
<223> OTHER INFORMATION: Amino acid at position 10 is 2-amino-isobutyric
      acid (Aib)
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 19

Leu Glu Gly Arg Glu Lys Val Arg Ala Xaa Ile Xaa Xaa Glu Gly Xaa
1               5                  10                  15

Ser Thr Trp Ser Lys Arg Lys Lys
            20

<210> SEQ ID NO 20
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is 2-amino-isobutyric
      acid (Aib)
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is alpha
      -Methyl-lysine (Mly)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 20

Leu Glu Gly Arg Glu Lys Val Arg Ala Xaa Ile Xaa Xaa Glu Gly Xaa
1               5                  10                  15
```

Ser Thr Trp Ser Xaa Arg Lys Lys
            20

<210> SEQ ID NO 21
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: Amino acid at position 24 is
      N-epsilon-Acetyl-lysine, 2-amino-4-acetamido-hexanoic acid (K(Ac))
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 21

Leu Glu Gly Arg Glu Lys Val Arg Ala Gln Ile Xaa Xaa Glu Gly Xaa
1               5                   10                  15

Ser Thr Trp Ser Xaa Arg Lys Xaa
            20

<210> SEQ ID NO 22
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16

```
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 22

Leu Glu Gly Arg Glu Lys Val Arg Ala Gln Ile Xaa Xaa Glu Gly Xaa
1               5                   10                  15

Ser Thr Trp Ala Xaa Arg Lys Lys
            20

<210> SEQ ID NO 23
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 23

Leu Glu Gly Arg Glu Lys Val Arg Ala Gln Ile Xaa Xaa Glu Gly Xaa
1               5                   10                  15

Ser Thr Trp Thr Xaa Arg Lys Lys
            20

<210> SEQ ID NO 24
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its
```

```
      N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 24

Leu Glu Gly Arg Glu Lys Val Arg Ala Xaa Ile Xaa Xaa Glu Gly Xaa
1               5                   10                  15

Ser Thr Trp Ser Xaa Arg Lys Lys
            20

<210> SEQ ID NO 25
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is
      N-epsilon-Acetyl-lysine, 2-amino-4-acetamido-hexanoic acid (K(Ac))
<220> FEATURE:
<221> NAME/KEY: VARIANT
```

-continued

```
<222> LOCATION: 25
<223> OTHER INFORMATION: The peptide is substituted with an -NH2 group
      on its C-terminal extremity

<400> SEQUENCE: 25

Leu Glu Gly Arg Glu Lys Val Arg Ala Xaa Ile Xaa Xaa Glu Gly Xaa
1               5                   10                  15

Ser Thr Trp Ser Xaa Arg Lys Lys Lys
            20                  25

<210> SEQ ID NO 26
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is
      N-epsilon-Acetyl-lysine, 2-amino-4-acetamido-hexanoic acid (K(Ac))
<220> FEATURE:
<221> NAME/KEY: VARIANT
<222> LOCATION: 25
<223> OTHER INFORMATION: Amino acid at position 25 is
      N-epsilon-Acetyl-lysine, 2-amino-4-acetamido-hexanoic acid (K(Ac))
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 26

Leu Glu Gly Arg Glu Lys Val Arg Ala Xaa Ile Xaa Xaa Glu Gly Xaa
1               5                   10                  15

Ser Thr Trp Ser Xaa Arg Lys Lys Xaa
            20                  25

<210> SEQ ID NO 27
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
```

```
            group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: Amino acid at position 24 is
      N-epsilon-Acetyl-lysine, 2-amino-4-acetamido-hexanoic acid (K(Ac))
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 27

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Lys
            20                  25

<210> SEQ ID NO 28
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
```

<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: Amino acid at position 24 is
      N-epsilon-Acetyl-lysine, 2-amino-4-acetamido-hexanoic acid (K(Ac))
<220> FEATURE:
<221> NAME/KEY: VARIANT
<222> LOCATION: 25
<223> OTHER INFORMATION: Amino acid at position 25 is
      N-epsilon-Acetyl-lysine, 2-amino-4-acetamido-hexanoic acid (K(Ac))
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 28

Leu Glu Gly Arg Glu Lys Val Arg Ala Xaa Ile Xaa Xaa Glu Gly Xaa
1               5                   10                  15

Ser Thr Trp Ser Xaa Arg Lys Xaa Xaa
            20                  25

<210> SEQ ID NO 29
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 19
<223> OTHER INFORMATION: Amino acid at position 19 is 1-Naphtylalanine
      (1-Nal)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: Amino acid at position 24 is
      N-epsilon-Acetyl-lysine, 2-amino-4-acetamido-hexanoic acid (K(Ac))
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 29

Leu Glu Gly Arg Glu Lys Val Arg Ala Xaa Ile Xaa Xaa Glu Gly Xaa
1               5                   10                  15

Ser Thr Xaa Ser Xaa Arg Lys Xaa
            20

<210> SEQ ID NO 30
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 20
<223> OTHER INFORMATION: Amino acid at position 20 is alpha
      -Methyl-serine (Mse)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: Amino acid at position 24 is
      N-epsilon-Acetyl-lysine, 2-amino-4-acetamido-hexanoic acid (K(Ac))
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 30

Leu Glu Gly Arg Glu Lys Val Arg Ala Xaa Ile Xaa Xaa Glu Gly Xaa
1               5                   10                  15

Ser Thr Trp Xaa Xaa Arg Lys Xaa
            20

<210> SEQ ID NO 31
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT

```
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 31

Leu Glu Gly Arg Glu Lys Val Arg Ala Xaa Ile Xaa Xaa Glu Gly Xaa
1               5                   10                  15

Ser Thr Trp Ser Xaa Arg Lys Gln
            20

<210> SEQ ID NO 32
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
```

```
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 32

Leu Glu Gly Arg Glu Lys Val Arg Ala Xaa Ile Xaa Xaa Glu Gly Xaa
1               5                   10                  15

Ser Thr Trp Ser Xaa Arg Lys Leu
            20

<210> SEQ ID NO 33
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Amino acid at position 9 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 33

Leu Glu Gly Arg Glu Lys Val Arg Xaa Gln Ile Xaa Xaa Glu Gly Xaa
1               5                   10                  15

Ser Thr Trp Ser Xaa Arg Lys Lys
            20

<210> SEQ ID NO 34
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
```

```
<222> LOCATION: 9
<223> OTHER INFORMATION: Amino acid at position 9 is
      N-epsilon-Acetyl-lysine, 2-amino-4-acetamido-hexanoic acid (K(Ac))
<220> FEATURE:
<221> NAME/KEY: VARIANT
<222> LOCATION: 10
<223> OTHER INFORMATION: Amino acid at position 10 is 2-amino-isobutyric
      acid (Aib)
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 34

Leu Glu Gly Arg Glu Lys Val Arg Xaa Xaa Ile Xaa Xaa Glu Gly Xaa
1               5                   10                  15

Ser Thr Trp Ser Xaa Arg Lys Lys
            20

<210> SEQ ID NO 35
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 35

Leu Glu Gly Arg Glu Lys Val Arg Ala Gln Ile Xaa Xaa Glu Gly Gln
1               5                   10                  15
```

Ser Thr Trp Ser Xaa Arg Lys Lys
            20

<210> SEQ ID NO 36
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 19
<223> OTHER INFORMATION: Amino acid at position 19 is 1-Naphtylalanine
      (1-Nal)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 36

Leu Glu Gly Arg Glu Lys Val Arg Ala Gln Ile Xaa Xaa Gly Gly Xaa
1               5                   10                  15

Ser Lys Xaa Ser Lys Arg
            20

<210> SEQ ID NO 37
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT

```
<222> LOCATION: 19
<223> OTHER INFORMATION: Amino acid at position 19 is 1-Naphtylalanine
      (1-Nal)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 37

Leu Glu Gly Arg Glu Lys Val Arg Ala Gln Ile Xaa Xaa Glu Gly Xaa
1               5                   10                  15

Ser Thr Xaa Ser Lys Arg
            20

<210> SEQ ID NO 38
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 38

Leu Glu Gly Arg Glu Lys Val Arg Ala Gln Ile Xaa Xaa Glu Gly Met
1               5                   10                  15

Ser Lys Trp Ser Lys Arg
            20

<210> SEQ ID NO 39
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 18
<223> OTHER INFORMATION: Amino acid at position 18 is alpha
```

-Methyl-serine (Mse)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 39

Leu Glu Gly Arg Glu Lys Val Arg Ala Gln Ile Xaa Xaa Glu Gly Met
1               5                   10                  15

Ser Xaa Trp Ser Lys Arg
            20

<210> SEQ ID NO 40
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 40

Leu Glu Gly Arg Glu Lys Val Arg Ala Gln Ile Xaa Xaa Glu Gly Met
1               5                   10                  15

Ser Thr Trp Ser Lys Arg
            20

<210> SEQ ID NO 41
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:

```
<221> NAME/KEY: VARIANT
<222> LOCATION: 22
<223> OTHER INFORMATION: The peptide is substituted with an -NH2 group
      on its C-terminal extremity

<400> SEQUENCE: 41

Leu Glu Gly Arg Glu Lys Val Arg Ala Gln Ile Xaa Xaa Glu Gly Met
1               5                   10                  15

Ser Thr Trp Ser Xaa Arg
            20

<210> SEQ ID NO 42
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 9
<223> OTHER INFORMATION: Amino acid at position 9 is 2-amino-isobutyric
      acid (Aib)
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 42

Leu Glu Gly Arg Glu Lys Val Arg Xaa Gln Ile Xaa Xaa Glu Gly Met
1               5                   10                  15

Ser Thr Trp Ser Xaa Arg
            20

<210> SEQ ID NO 43
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is 2-amino-isobutyric
      acid (Aib)
<220> FEATURE:
<221> NAME/KEY: VARIANT
<222> LOCATION: 12
```

<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 43

Leu Glu Gly Arg Glu Lys Val Arg Ala Xaa Ile Xaa Xaa Glu Gly Met
1               5                   10                  15

Ser Thr Trp Ser Xaa Arg
            20

<210> SEQ ID NO 44
<211> LENGTH: 23
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 23
<223> OTHER INFORMATION: The peptide is substituted with an -NH2 group
      on its C-terminal extremity

<400> SEQUENCE: 44

Leu Glu Gly Arg Glu Lys Val Arg Ala Gln Ile Xaa Xaa Glu Gly Xaa
1               5                   10                  15

Ser Thr Trp Ser Xaa Arg Lys
            20

<210> SEQ ID NO 45
<211> LENGTH: 23
<212> TYPE: PRT
<213> ORGANISM: Artificial Sequence
<220> FEATURE:
<223> OTHER INFORMATION: Peptide analogue of the B-chain of Relaxin-2

```
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 23
<223> OTHER INFORMATION: The peptide is substituted with an -NH2 group
      on its C-terminal extremity

<400> SEQUENCE: 45

Leu Glu Gly Arg Glu Lys Val Arg Ala Gln Ile Xaa Xaa Glu Gly Met
1               5                   10                  15

Ser Thr Trp Ser Xaa Arg Lys
            20

<210> SEQ ID NO 46
<211> LENGTH: 22
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 22
<223> OTHER INFORMATION: The peptide is substituted with an -NH2 group
      on its C-terminal extremity

<400> SEQUENCE: 46

Leu Glu Gly Arg Glu Lys Val Arg Ala Gln Ile Xaa Xaa Glu Gly Met
1               5                   10                  15

Ser Lys Trp Ser Xaa Arg
            20

<210> SEQ ID NO 47
<211> LENGTH: 23
<212> TYPE: PRT
```

```
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 23
<223> OTHER INFORMATION: The peptide is substituted with an -NH2 group
      on its C-terminal extremity

<400> SEQUENCE: 47

Leu Glu Gly Arg Glu Lys Val Arg Ala Xaa Ile Xaa Xaa Glu Gly Xaa
1               5                   10                  15

Ser Thr Trp Ser Xaa Arg Lys
            20

<210> SEQ ID NO 48
<211> LENGTH: 25
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 14
<223> OTHER INFORMATION: Amino acid at position 14 is 2-amino-isobutyric
      acid (Aib)
<220> FEATURE:
<221> NAME/KEY: VARIANT
<222> LOCATION: 17
<223> OTHER INFORMATION: Amino acid at position 17 is 2-amino hexanoic
      acid (Norleucine, Nle)
<220> FEATURE:
<221> NAME/KEY: VARIANT
<222> LOCATION: 22
<223> OTHER INFORMATION: Amino acid at position 22 is 2-amino-isobutyric
      acid (Aib)
```

```
<220> FEATURE:
<221> NAME/KEY: VARIANT
<222> LOCATION: 25
<223> OTHER INFORMATION: The peptide is substituted with an -NH2 group
      on its C-terminal extremity

<400> SEQUENCE: 48

Glu Leu Glu Gly Arg Glu Lys Val Arg Ala Ala Ile Xaa Xaa Glu Gly
1               5                   10                  15

Xaa Ser Thr Trp Ser Xaa Arg Lys Lys
            20                  25

<210> SEQ ID NO 49
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 49

Leu Glu Gly Arg Glu Lys Val Arg Arg Gln Ile Xaa Xaa Glu Gly Xaa
1               5                   10                  15

Ser Thr Trp Ser Xaa Arg Lys Lys
            20

<210> SEQ ID NO 50
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
```

```
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 50

Leu Glu Gly Arg Glu Lys Val Arg Ala Gln Ile Xaa Xaa Glu Gly Xaa
1               5                   10                  15

Ser Thr Trp Ser Xaa Arg Arg Arg
            20

<210> SEQ ID NO 51
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 51

Leu Glu Gly Arg Glu Lys Val Arg Ala Gln Ile Xaa Xaa Glu Gly Xaa
1               5                   10                  15

Ser Thr Phe Ser Xaa Arg Lys Lys
            20

<210> SEQ ID NO 52
<211> LENGTH: 24
<212> TYPE: PRT
<213> ORGANISM: Artificial Sequence
<220> FEATURE:
```

<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 52

Leu Glu Gly Arg Glu Lys Val Arg Ala Gln Ile Xaa Xaa Glu Gly Xaa
1               5                   10                  15

Ser Gln Trp Ser Xaa Arg Arg Arg
            20

<210> SEQ ID NO 53
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 53

```
Leu Glu Gly Arg Glu Lys Val Arg Ala Gln Ile Xaa Xaa Glu Gly Xaa
1               5                   10                  15

Ser Thr

```
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 55

Leu Glu Gly Arg Glu Lys Val Arg Ala Gln Ile Xaa Xaa Glu Gly Xaa
1               5                   10                  15

Ser Arg Trp Ser Xaa Arg Arg Arg
            20

<210> SEQ ID NO 56
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 1
<223> OTHER INFORMATION: Amino acid at position 1 is
      alpha-Methyl-leucine (Mel)
<220> FEATURE:
<221> NAME/KEY: VARIANT
<222> LOCATION: 10
<223> OTHER INFORMATION: Amino acid at position 10 is
      N-epsilon-Acetyl-lysine, 2-amino-4-acetamido-hexanoic acid (K(Ac))
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 16
<223> OTHER INFORMATION: Amino acid at position 16 is 2-amino hexanoic
      acid (Norleucine, Nle)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: Amino acid at position 24 is
      N-epsilon-Acetyl-lysine, 2-amino-4-acetamido-hexanoic acid (K(Ac))
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 56

Xaa Glu Gly Arg Glu Lys Val Arg Ala Xaa Ile Xaa Xaa Glu Gly Xaa
1               5                   10                  15

Ser Thr Trp Ser Xaa Arg Lys Xaa
            20

<210> SEQ ID NO 57
<211> LENGTH: 24
```

```
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal
      extremity

<400> SEQUENCE: 57

Leu Glu Gly Arg Glu Lys Val Arg Ala Gln Ile Xaa Xaa Glu Gly Gln
1               5                   10                  15

Ser Thr Phe Ser Xaa Arg Lys Lys
            20

<210> SEQ ID NO 58
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 58

Leu Glu Gly Arg Glu Lys Val Arg Ala Gln Ile Xaa Xaa Glu Gly Gln
1               5                   10                  15

Ser Thr Tyr Ser Xaa Arg Lys Lys
            20
```

```
<210> SEQ ID NO 59
<211> LENGTH: 24
<212> TYPE: PRT
<213> ORGANISM: Artificial Sequence
<220> FEATURE:
<223> OTHER INFORMATION: Peptide analogue of the B-chain of Relaxin-2
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 12
<223> OTHER INFORMATION: Amino acid at position 12 is 2-amino-isobutyric
      acid (Aib)
<220> FEATURE:
<221> NAME/KEY: VARIANT
<222> LOCATION: 13
<223> OTHER INFORMATION: Amino acid at position 13 is 2-amino-isobutyric
      acid (Aib)
<220> FEATURE:
<221> NAME/KEY: VARIANT
<222> LOCATION: 19
<223> OTHER INFORMATION: Amino acid at position 19 is
      4-Fluoro-phenylalanine (Pfp)
<220> FEATURE:
<221> NAME/KEY: VARIANT
<222> LOCATION: 21
<223> OTHER INFORMATION: Amino acid at position 21 is 2-amino-isobutyric
      acid (Aib)
<220> FEATURE:
<221> NAME/KEY: VARIANT
<222> LOCATION: 24
<223> OTHER INFORMATION: The peptide is substituted with an -NH2 group
      on its C-terminal extremity

<400> SEQUENCE: 59

Leu Glu Gly Arg Glu Lys Val Arg Ala Gln Ile Xaa Xaa Glu Gly Gln
1               5                   10                  15

Ser Thr Xaa Ser Xaa Arg Lys Lys
            20

<210> SEQ ID NO 60
<211> LENGTH: 24
<212> TYPE: PRT
<213> ORGANISM: Artificial Sequence
<220> FEATURE:
<223> OTHER INFORMATION: H2-relaxin A chain
<220> FEATURE:
<221> NAME/KEY: VARIANT
<222> LOCATION: 1
<223> OTHER INFORMATION: The peptide is substituted with a hydrogen atom
      (H) on its N-terminal extremity

<400> SEQUENCE: 60

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 61
<211> LENGTH: 29
<212> TYPE: PRT
<213> ORGANISM: Artificial Sequence
<220> FEATURE:
<223> OTHER INFORMATION: H2-relaxin B chain
<220> FEATURE:
<221> NAME/KEY: VARIANT
<222> LOCATION: 1
<223> OTHER INFORMATION: The peptide is substituted with a hydrogen atom
```

(H) on its N-terminal extremity

<400> SEQUENCE: 61

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 62
<211> LENGTH: 27
<212> TYPE: PRT
<213> ORGANISM: Artificial Sequence
<220> FEATURE:
<223> OTHER INFORMATION: Peptide analogue of the B-chain of Relaxin-2-
      comparison example
<220> FEATURE:
<221> NAME/KEY: VARIANT
<222> LOCATION: 1
<223> OTHER INFORMATION: The peptide is substituted with a hydrogen atom
      (H) on its N-terminal extremity
<220> FEATURE:
<221> NAME/KEY: VARIANT
<222> LOCATION: 27
<223> OTHER INFORMATION: The peptide is substituted with an -NH2 group
      on its C-terminal extremity

<400> SEQUENCE: 62

Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25

<210> SEQ ID NO 63
<211> LENGTH: 27
<212> TYPE: PRT
<213> ORGANISM: Artificial Sequence
<220> FEATURE:
<223> OTHER INFORMATION: Peptide analogue of the B-chain of Relaxin-2-
      comparison example
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT
<222> LOCATION: 27
<223> OTHER INFORMATION: The peptide is substituted with an -NH2 group
      on its C-terminal extremity

<400> SEQUENCE: 63

Val Ile Lys Leu Ser Gly Arg Glu Leu Val Arg Ala Gln Ile Ala Ile
1               5                   10                  15

Ser Gly Met Ser Thr Trp Ser Lys Arg Ser Leu
            20                  25

<210> SEQ ID NO 64
<211> LENGTH: 27
<212> TYPE: PRT
<213> ORGANISM: Artificial Sequence
<220> FEATURE:
<223> OTHER INFORMATION: Peptide analogue of the B-chain of Relaxin-2-
      comparison example
<220> FEATURE:
<221> NAME/KEY: VARIANT
<222> LOCATION: 1
<223> OTHER INFORMATION: The peptide is substituted with an acetyl (Ac)
      group on its N-terminal extremity
<220> FEATURE:
<221> NAME/KEY: VARIANT

```
<222> LOCATION: 27
<223> OTHER INFORMATION: The peptide is substituted with an -NH2 group
      on its C-terminal extremity

<400> SEQUENCE: 64

Val Ile Lys Leu Ser Gly Arg Glu Leu Val Arg Ala Gln Ile Ala Ile
1               5                   10                  15

Ser Gly Met Ser Thr Trp Ser Lys Lys Lys
            20                  25

<210> SEQ ID NO 65
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Peptide is substituted with hydrogen atom or
      acetyl group on its N-terminal extremity and can be absent
<220> FEATURE:
<221> NAME/KEY: VARIANT
<222> LOCATION: 2
<223> OTHER INFORMATION: Xaa represents an amino acid selected from the
      group consisting of leucine, 2-amino-isobutyric acid,
      alpha-methyl-leucine and N-epsilon-acetyl-lysine
<220> FEATURE:
<221> NAME/KEY: VARIANT
<222> LOCATION: 7
<223> OTHER INFORMATION: Xaa represents an amino acid selected from the
      group consisting of lysine, homolysine, arginine, homoarginine
      and ornithine
<220> FEATURE:
<221> NAME/KEY: VARIANT
<222> LOCATION: 10
<223> OTHER INFORMATION: Xaa represents an amino acid selected from the
      group consisting of alanine, 2-amino-isobutyric acid,
      N-epsilon-acetyl-lysine, arginine, leucine and glutamine
<220> FEATURE:
<221> NAME/KEY: VARIANT
<222> LOCATION: 11
<223> OTHER INFORMATION: Xaa represents an amino acid selected from the
      group consisting of glutamine, N-epsilon-acetyl-lysine, alanine
      and 2-amino-isobutyric acid
<220> FEATURE:
<221> NAME/KEY: VARIANT
<222> LOCATION: 13
<223> OTHER INFORMATION: Xaa represents an amino acid selected from the
      group consisting of alanine and 2-amino-isobutyric acid
<220> FEATURE:
<221> NAME/KEY: VARIANT
<222> LOCATION: 14
<223> OTHER INFORMATION: Xaa represents an amino acid selected from the
      group consisting of isoleucine and 2-amino-isobutyric acid
<220> FEATURE:
<221> NAME/KEY: VARIANT
<222> LOCATION: 17
<223> OTHER INFORMATION: Xaa represents an amino acid selected from the
      group consisting of methionine, norleucine, glutamine, glutamic
      acid and N-epsilon-acetyl-lysine
<220> FEATURE:
<221> NAME/KEY: VARIANT
<222> LOCATION: 19
<223> OTHER INFORMATION: Xaa represents an amino acid selected from the
      group consisting of threonine, lysine, alpha-methyl-serine,
      glutamine and arginine
<220> FEATURE:
<221> NAME/KEY: VARIANT
<222> LOCATION: 20
<223> OTHER INFORMATION: Xaa represents an amino acid selected from the
      group consisting of tryptophan, 5-chlorotryptophan,
      5-Fluorotryptophan,
<220> FEATURE:
<221> NAME/KEY: VARIANT
<222> LOCATION: 20
```

```
<223> OTHER INFORMATION: ...5-MethoxyTryptophan, phenylalanine,
      homophenylalanine, tyrosine, 4-fluoro-phenylalanine,
      1-naphtylalanine and 2-naphtylalanine.
<220> FEATURE:
<221> NAME/KEY: VARIANT
<222> LOCATION: 21
<223> OTHER INFORMATION: Xaa represents an amino acid selected from the
      group consisting of serine, alanine, threonine,
      alpha-methyl-serine, N-epsilon-acetyl-lysine and valine
<220> FEATURE:
<221> NAME/KEY: VARIANT
<222> LOCATION: 22
<223> OTHER INFORMATION: Xaa represents an amino acid selected from the
      group consisting of lysine, 2-amino-isobutyric acid,
      alpha-methyl-lysine, N-epsilon-acetyl-lysine and arginine
<220> FEATURE:
<221> NAME/KEY: VARIANT
<222> LOCATION: 24
<223> OTHER INFORMATION: Xaa represents an amino acid selected from the
      group consisting of lysine, arginine and N-epsilon-acetyl-lysine
      and can be absent
<220> FEATURE:
<221> NAME/KEY: VARIANT
<222> LOCATION: 25
<223> OTHER INFORMATION: Xaa represents an amino acid selected from the
      group consisting of leucine, lysine, N-epsilon-acetyl-lysine,
      glutamine, arginine and alanine and can be absent
<220> FEATURE:
<221> NAME/KEY: VARIANT
<222> LOCATION: 26
<223> OTHER INFORMATION: Xaa represents an amino acid selected from the
      group consisting of lysine and N-epsilon-acetyl-lysine and can
      be absent
<220> FEATURE:
<221> NAME/KEY: VARIANT
<222> LOCATION: 26
<223> OTHER INFORMATION: The peptide is substituted with an -NH2 group
      on its C-terminal extremity

<400> SEQUENCE: 65

Glu Xaa Glu Gly Arg Glu Xaa Val Arg Xaa Xaa Ile Xaa Xaa Glu Gly
1               5                   10                  15

Xaa Ser Xaa Xaa Xaa Xaa Arg Xaa Xaa Xaa
            20                  25

<210> SEQ ID NO 66
<211> LENGTH: 26
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Peptide is substituted with hydrogen atom or
      acetyl group on its N-terminal extremity and can be absent
<220> FEATURE:
<221> NAME/KEY: VARIANT
<222> LOCATION: 2
<223> OTHER INFORMATION: represents an amino acid selected from the
      group consisting of leucine, 2-amino-isobutyric acid and
      alpha-methyl-leucine
<220> FEATURE:
<221> NAME/KEY: VARIANT
<222> LOCATION: 10
<223> OTHER INFORMATION: Xaa represents an amino acid selected from the
      group consisting of alanine, 2-amino-isobutyric acid,
      N-epsilon-acetyl-lysine and arginine
<220> FEATURE:
<221> NAME/KEY: VARIANT
<222> LOCATION: 11
<223> OTHER INFORMATION: Xaa represents an amino acid selected from the
      group consisting of glutamine, N-epsilon-acetyl- lysine, alanine
      and 2-amino-isobutyric acid
<220> FEATURE:
<221> NAME/KEY: VARIANT
```

```
<222> LOCATION: 13
<223> OTHER INFORMATION: Xaa 2-amino-isobutyric acid
<220> FEATURE:
<221> NAME/KEY: VARIANT
<222> LOCATION: 14
<223> OTHER INFORMATION: Xaa represents an amino acid selected from the
      group consisting of isoleucine and 2-amino-isobutyric acid
<220> FEATURE:
<221> NAME/KEY: VARIANT
<222> LOCATION: 17
<223> OTHER INFORMATION: Xaa represents an amino acid selected from the
      group consisting of methionine, norleucine and glutamine
<220> FEATURE:
<221> NAME/KEY: VARIANT
<222> LOCATION: 19
<223> OTHER INFORMATION: Xaa represents an amino acid selected from the
      group consisting of threonine, lysine, alpha-methyl-serine,
      glutamine and arginine
<220> FEATURE:
<221> NAME/KEY: VARIANT
<222> LOCATION: 20
<223> OTHER INFORMATION: Xaa represents an amino acid selected from the
      group consisting of tryptophan, 1-naphtylalanine, phenylalanine,
      tyrosine and 4-fluoro-phenylalanine
<220> FEATURE:
<221> NAME/KEY: VARIANT
<222> LOCATION: 21
<223> OTHER INFORMATION: Xaa represents an amino acid selected from the
      group consisting of serine, alanine, threonine and
      alpha-methyl-serine
<220> FEATURE:
<221> NAME/KEY: VARIANT
<222> LOCATION: 22
<223> OTHER INFORMATION: Xaa represents an amino acid selected from the
      group consisting of lysine, 2-amino-isobutyric acid,
      alpha-methyl-lysine and N-epsilon-acetyl-lysine
<220> FEATURE:
<221> NAME/KEY: VARIANT
<222> LOCATION: 24
<223> OTHER INFORMATION: Xaa represents an amino acid selected from the
      group consisting of lysine and arginine and can be absent
<220> FEATURE:
<221> NAME/KEY: VARIANT
<222> LOCATION: 25
<223> OTHER INFORMATION: Xaa represents an amino acid selected from the
      group consisting of leucine, lysine, N-epsilon-acetyl-lysine,
      glutamine and arginine and can be absent
<220> FEATURE:
<221> NAME/KEY: VARIANT
<222> LOCATION: 26
<223> OTHER INFORMATION: Xaa represents an amino acid selected from the
      group consisting of lysine and N-epsilon-acetyl-lysine and can
      be absent
<220> FEATURE:
<221> NAME/KEY: VARIANT
<222> LOCATION: 26
<223> OTHER INFORMATION: The peptide is substituted with an -NH2 group
      on its C-terminal extremity

<400> SEQUENCE: 66

Glu Xaa Glu Gly Arg Glu Lys Val Arg Xaa Xaa Ile Xaa Xaa Glu Gly
1               5                   10                  15

Xaa Ser Xaa Xaa Xaa Xaa Arg Xaa Xaa Xaa
            20                  25

<210> SEQ ID NO 67
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2, 3, 4, 6, 7
<223> OTHER INFORMATION: Xaa = Any Amino Acid
<220> FEATURE:
```

```
<221> NAME/KEY: VARIANT
<222> LOCATION: 8
<223> OTHER INFORMATION: Xaa = Ile or Val

<400> SEQUENCE: 67

Arg Xaa Xaa Xaa Arg Xaa Xaa Xaa
1               5
```